US012297222B2

(12) United States Patent
Ralph et al.

(10) Patent No.: US 12,297,222 B2
(45) Date of Patent: May 13, 2025

(54) CD206 TARGETED DRUG DELIVERY VEHICLES CARRYING NOVEL BISPHOSPHONATE DRUG PAYLOADS VIA A DEGRADABLE LINKER

(71) Applicant: Navidea Biopharmaceuticals, Inc., Columbus, OH (US)

(72) Inventors: David A. Ralph, Columbus, OH (US); Jeffrey Scott Arnold, Andover, MA (US)

(73) Assignee: Navidea Biopharmaceuticals, Inc., Columbus, OH (US)

( * ) Notice: Subject to any disclaimer, the term of this patent is extended or adjusted under 35 U.S.C. 154(b) by 0 days.

(21) Appl. No.: 18/664,971

(22) Filed: May 15, 2024

(65) Prior Publication Data

US 2024/0294564 A1 Sep. 5, 2024

Related U.S. Application Data

(62) Division of application No. 18/320,431, filed on May 19, 2023, now Pat. No. 12,006,339.

(60) Provisional application No. 63/352,324, filed on Jun. 15, 2022, provisional application No. 63/344,134, filed on May 20, 2022.

(51) Int. Cl.
*C07H 13/12* (2006.01)
*A61K 45/06* (2006.01)
*A61K 47/61* (2017.01)
*C07F 9/6539* (2006.01)

(52) U.S. Cl.
CPC ............. *C07H 13/12* (2013.01); *A61K 45/06* (2013.01); *A61K 47/61* (2017.08); *C07F 9/65397* (2013.01)

(58) Field of Classification Search
None
See application file for complete search history.

(56) References Cited

U.S. PATENT DOCUMENTS

| | | | |
|---|---|---|---|
| 6,036,963 | A | 3/2000 | Weinkauf et al. |
| 7,666,979 | B2 | 2/2010 | Fan et al. |
| 8,071,573 | B2 * | 12/2011 | Sanders .................. A61P 37/00 546/22 |
| 10,792,582 | B2 | 10/2020 | Qin et al. |
| 2004/0116348 | A1 | 6/2004 | Chau et al. |
| 2004/0122382 | A1 | 6/2004 | Johnson et al. |
| 2005/0042248 | A1 | 2/2005 | Ahmad et al. |
| 2005/0214859 | A1 | 9/2005 | Dransfield et al. |
| 2009/0004218 | A1 | 1/2009 | Hacohen et al. |
| 2009/0311182 | A1 | 12/2009 | Wang et al. |
| 2010/0261875 | A1 | 10/2010 | Dransfield et al. |
| 2013/0330274 | A1 | 12/2013 | Berr et al. |
| 2014/0127301 | A1 | 5/2014 | Alexis et al. |
| 2014/0235790 | A1 | 8/2014 | Stayton et al. |
| 2015/0023876 | A1 | 1/2015 | Cope et al. |
| 2019/0321465 | A1 | 10/2019 | Zhang et al. |
| 2020/0306381 | A1 | 10/2020 | Ralph |

FOREIGN PATENT DOCUMENTS

| | | |
|---|---|---|
| GB | 1069820 A | 5/1967 |
| JP | 2012516328 A | 7/2012 |
| WO | 9608263 A1 | 3/1996 |
| WO | 2012169973 A1 | 12/2012 |
| WO | 2015013341 A1 | 1/2015 |
| WO | 2016011415 A2 | 1/2016 |
| WO | 2016011419 A1 | 1/2016 |

OTHER PUBLICATIONS

Allavena, P., et al., "Engagement of the man nose receptor by tumoral mucins activates an immune suppressive phenotype in human tumor-associated macrophages," Clin. Dev. Immunol. 2010: 547179.
Azad, A. K., et al., "Exploitation of the Macrophage Mannose Receptor (CD206) in Infectious Disease Diagnostics and Therapeutics," J. Cytol. Mol. Biol. 1, Jan. 10, 2014, 10 pages.
Balkwill, F., et al., "Inflammation and cancer: back to Virchow?" Lancet 357: 2001, pp. 539-545.
Banerji, S., et al., "LYVE-1, a new homologue of the CD44 glycoprotein, is a lymph-specific receptor for Hyaluronan," J Cell Biol. 144: 1999, pp. 789-801.
Beasley, N. J., et al., "Intratumoral lymphangiogenesis and lymph node metastasis in head and neck cancer," Cancer Res. 62: 2002, pp. 1315-1320.
Choe et al., "Targeted In Vivo Imaging of Angiogenesis: Present Status and Perspectives," 2007, Current Pharmaceutical Design, 13:17-31.
Choi, Y. K., et al., "Characterization of cells expressing lymphatic marker LYVE-1 in macaque large intestine during simian immunodeficiency virus infection identifies a large population of non-vascular LYVE-1(+)/DC-SIGN(+) cells," Lymphat. Res. Biol. 11: 2013, pp. 26-34.
Coessens et al., "Synthesis of polyglutamine and dextran conjugates of streptomycin with an acid-sensitive drug-carrier linkage," Journal of Controlled Release, 1996, vol. 38, No. 2, pp. 141-150.

(Continued)

*Primary Examiner* — Patrick T Lewis
(74) *Attorney, Agent, or Firm* — Fredrikson & Byron, P.A.

(57) ABSTRACT

Provided are novel compounds containing a polymeric carbohydrate backbone, one or more mannose-binding C-type lectin receptor targeting moieties, and a nitrogenous bisphosphonate compound coupled to the backbone via a thiol-maleimide conjugation, in addition to pharmaceutical compositions, methods of synthesizing, and methods of use. The thiol-maleimide conjugation of a bisphosphonate to a polymeric carbohydrate backbone provides for methods of using the compounds and compositions thereof for releasing the therapeutic payload when internalized into a mannose-binding C-type lectin receptor-expressing cell, such as tumor associated macrophages (TAMs) for the treatment of various diseases, including, cancer, autoimmune diseases, and inflammatory disorders.

13 Claims, 9 Drawing Sheets

(56) References Cited

OTHER PUBLICATIONS

Coughlin, A., et al., "Oral cavity squamous cell carcinoma and the clinically n0 neck: the past, present, and future of sentinel lymph node biopsy," Curr. Oncol. Rep. 12: 2010, pp. 129-135.
Dave, S.S., et al., "Molecular diagnosis of Burkitt's lymphoma," N. Engl. J. Med. 354: 2006, pp. 2431-2442.
Dijkgraaf et al., "Molecular imaging of angiogenesis with SPECT," 2010, Eur. J. Nucl. Med. Mol. Imaging, published online Sep. 21, 2010.
Ellner, S. J., et al., "Dose-dependent biodistribution of [(99m)Tc]DTPA-mannosyl-dextran for breast cancer sentinel lymph node mapping," Nucl. Med. Biol. 30: 2003, pp. 805-810.
Ellner, S. J., et al., "Sentinel lymph node mapping of the colon and stomach using lymphoseek in a pig model," Ann. Surg. Oncol. 11: 2004, pp. 674-681.
Emerson et al., "A Receptor-targeted Fluorescent Radiopharmaceutical for Multireporter Sentinel Lymph Node Imaging," Radiology, 2012, 265(1):186-193.
Engering, A., et al., "The dendritic cell-specific adhesion receptor DC-SIGN internalizes antigen for presentation to T cells," J. Immunol. 168: 2002, pp. 2118-2126.
Farinha, P., et al., "The architectural pattern of FOXP3-positive T cells in follicular lymphoma is an independent predictor of survival and histologic transformation," Blood, 115: 2010, pp. 289-295.
Gazi, U., et al., "Influence of the mannose receptor in host immune responses," Immunobiology 214: 2009, pp. 554-561.
Geijtenbeek, T. B., et al., "Self- and nonself-recognition by C-type lectins on dendritic cells," Annu. Rev. Immunol. 22: 2004, pp. 33-54.
Gordon, S., "Alternative activation of macrophages," Nat. Rev. Immunol. 3: 2003, pp. 23-35.
Gordon, S., "Pattern recognition receptors: doubling up for the innate immune response," Cell 111: 2002, pp. 927-930.
Hattori, Y., et al., "Enhanced DNA vaccine potency by mannosylated lipoplex after intraperitoneal administration," J Gene Med 8: 2006, pp. 824-834.
Henning, L. N., et al., "Pulmonary surfactant protein A regulates TLR expression and activity in human macrophages," J. Immunol. 180: 2008, pp. 7847-7858.
Hoh, C. K., et al., "Preclinical studies of [(99m)Tc]DTPA-mannosyl-Dextran," Nucl. Med. Biol. 30: 2003, pp. 457-464.
Hongjing et al., "Facile preparation and drug delivery behaviour of novel dextran-based nanogels conjugated with doxorubicin via a pH-labile bond," Journal of Controlled Release, 2013, vol. 172, No. 1, pp. e67-e68.
Jarjour et al., "Fluorescent CD206-targeted Manocept-Cy3 (Mano-Cy3) specifically localizes on macrophages (MPs) derived from rheumatoid arthritis (RA) patients' synovial fluid & is quantitatively greater than that from non-RA patients," J Nucl Med, 2014, 55(1):1229.
Jensen, T. O., et al., "Macrophage markers in serum and tumor have prognostic impact in American Joint Committee on Cancer stage I/II melanoma," J. Clin. Oncol. 27: 2009, pp. 3330-3337.
Kamper, P., et al., "Tumor-infiltrating macrophages correlate with adverse prognosis and Epstein-Barr virus status in classical Hodgkin's lymphoma," Haematologica 96: 2011, pp. 269-276.
Kang, B. K., et al., "The human macrophage mannose receptor directs *Mycobacterium tuberculosis* lipoarabinomannan-mediated phagosome biogenesis," J Exp. Med 202: 2005, pp. 987-999.
Kawakami, S., et al., "Mannose receptor-mediated gene transfer into macrophages using novel mannosylated cationic liposomes," Gene Ther. 7: 2000, pp. 292-299.
Kurahara, H., et al., "Significance of M2-polarized tumor-associated macrophage in pancreatic cancer," J. Surg. Res. 167: 2011, pp. e211-e219.
Lau, S. K., et al., "CD163: a specific marker of macrophages in paraffin-embedded tissue samples," Am. J. Clin. Pathol. 122: 2004, pp. 794-801.
Law, S. K. A., et al., "A new macrophage differentiation antigen which is a member of the scavenger receptor superfamily," Eur. J. Immunol. 23: 1993, pp. 2320-2325.

Lee, C. H., et al., "Prognostic significance of macrophage infiltration in leiomyosarcomas," Clin. Cancer Res. 14: 2008, pp. 1423-1430.
Lee, S. J., et al., "Mannose receptor-mediated regulation of serum glycoprotein Homeostasis," Science 295: 2002, p. 1901.
Leek, R. D., et al., "Association of macrophage infiltration with angiogenesis and prognosis in invasive breast carcinoma," Cancer Res. 56: 1996, pp. 4625-4629.
Leong, S. P., et al., "A phase 2 study of (99m)Tc-tilmanocept in the detection of sentinel lymph nodes in melanoma and breast cancer," Ann. Surg. Oncol. 18: 2011, pp. 961-969.
Leon-Rodriguez et al., "The Synthesis and Chelation Chemistry of DOTA-Peptide Conjugates," Bioconjugate Chemistry, Jan. 3, 2008, 19(2):391-402.
Li et al., "Cu-Labeled Tetrameric and Octameric RGD Peptides for Small-Animal PET of Tumor avb3 Integrin Expression," 2007, J. Nuclear Medicine, 48:1162-1171.
Li et al., "Synthesis and characterization of a high-affinity αvß6-specific ligand for in vitro and in vivo applications," 2009, Mol. Cancer Ther., 8:5:1239-1249.
Locke, L. W., et al., "PET imaging of tumor associated macrophages using mannose coated 64Cu liposomes," Biomaterials 33: 2012, pp. 7785-7793.
Irjala, H., et al., "Mannose receptor (MR) and common lymphatic endothelial and vascular endothelial receptor (CLEVER)-1 direct the binding of cancer cells to the lymph vessel endothelium," Cancer Res. 63: 2003, pp. 4671-4676.
Irjala, H., et al., "Mannose receptor is a novel ligand for L-selectin and mediates lymphocyte binding to lymphatic endothelium," J. Exp. Med. 194: 2001, pp. 1033-1042.
Lu, Y., et al., "Development of an antigen-presenting cell-targeted DNA vaccine against melanoma by mannosylated liposomes," Biomaterials 28: 2007, pp. 3255-3262.
Luo, Y., et al., "Targeting tumor-associated macrophages as a novel strategy against breast cancer," J. Clin. Invest 116: 2006, pp. 2132-2141.
Mantovani, A., et al., "Macrophage polarization: tumor-associated macrophages as a paradigm for polarized M2 mononuclear phagocytes," Trends Immunol. 23: 2002, pp. 549-555.
Mantovani, A., et al., "The origin and function of tumor-associated macrophages," Immunol. Today 13: 1992, pp. 265-270.
Marttila-Ichihara, F., et al., "Macrophage mannose receptor on lymphatics controls cell trafficking," Blood 112: 2008, pp. 64-72.
Mattila, M. M., et al., "VEGF-C induced lymphangiogenesis is associated with lymph node metastasis in orthotopic MCF-7 tumors," Int. J Cancer 98: 2002, pp. 946-951.
Maula, S. M., et al., "Intratumoral lymphatics are essential for the metastatic spread and prognosis in squamous cell carcinomas of the head and neck region," Cancer Res. 63: 2003, pp. 1920-1926.
McGrath et al., "CD206-targeted Cy3-Manocept (Mano-Cy3) localizes in nearly all cells present in Kaposi's sarcoma representing an opportunity for dynamic imaging, local staging and a potential for visceral metastasis imaging", Journal of Nuclear Medicine, 2014, 55(1):1681.
Mendez, J., et al., "Detection of gastric and colonic sentinel nodes through endoscopic administration of 99mTc-DTPA-mannosyl-dextran in pigs," J. Nucl. Med. 44: 2003, pp. 1677-1681.
Miller et al., "The Mannose Receptor Mediates Dengue Virus Infection of Macrophages," PLoS. Pathogens, vol. 4, Feb. 2008, Issue 2, 11 pages.
Mills, C. D., et al., "M-1/M-2 macrophages and the Th1/Th2 paradigm," J. Immunol. 164: 2000, pp. 6166-6173.
Movahedi, K., et al., "Nanobodybased targeting of the macrophage mannose receptor for effective in vivo imaging of tumorassociated macrophages," Cancer Res. 72: 2012, pp. 4165-4177.
Nahrendorf et al., "F-4V for PET-CT imaging of VCAM-1 expression in inflammatory atherosclerosis," 2009, JACC Cardiovasc. Imaging, 2:10:1213-1222.
Park, S. M., et al., "Mapping the distinctive populations of lymphatic endothelial cells in different zones of human lymph nodes," PLoS. One. 9: 2014, e94781.
Paul C.B., Tertiary Pharmacology Review, Center For Drug Evaluation and Research, Aug. 10, 2011, 134 pages.

(56) References Cited

OTHER PUBLICATIONS

Petrova, T. V., et al., "Lymphatic endothelial reprogramming of vascular endothelial cells by the Prox-1 homeobox transcription factor," EMBO J 21: 2002, pp. 4593-4599.
Podgrabinska, S., et al., "Molecular characterization of lymphatic endothelial cells," Proc. Natl. Acad. Sci. U.S. A 99: 2002, pp. 16069-16074.
Porcheray F., et al., "Macrophage Activation and Human Immunodeficiency Virus Infection: HIV Replication Directs Macrophages towards a Pro-Inflammatory Phenotype While Previous Activation Modulates Macrophage Susceptibility to Infection and Viral Production," Virology, 2006, vol. 349 (1), pp. 112-120.
Puig-Kroger, A., et al., "Regulated expression of the pathogen receptor dendritic cell-specific intercellular adhesion molecule 3 (ICAM-3)-grabbing nonintegrin in THP-1 human leukemic cells, monocytes, and macrophages," J Biol Chem 279: 2004, pp. 25680-25688.
Rajaram, M. V., et al., "*Mycobacterium tuberculosis* activates human macrophage peroxisome proliferator-activated receptor gamma linking mannose receptor recognition to regulation of immune responses," J Immunol. 185: 2010, pp. 929-942.
Rajaram, M. V., et al., "*Mycobacterium tuberculosis* lipomannan blocks TNF biosynthesis by regulating macrophage MAPK-activated protein kinase 2 (MK2) and microRNA miR-125b," Proc. Natl. Acad. Sci. U.S. A 108: 2011, pp. 17408-17413.
Roseeuw et al., "Synthesis, Degradation, and Antimicrobial Properties of Targeted Macromolecular Prodrugs of Norfloxacin," Antimicrobial Agents and Chemotherapy, 2003, vol. 47, No. 11, pp. 3435-3441.
Rosol et al., "Intravenous administration (IV) of the CD206-targeted Manocept-Cy3 (Mano-Cy3) to mice with induced rheumatoid arthritis (RA) results in heterogeneous localization of Mano-Cy3 with strong specificity for RA-expressing joints," J Nucl Med, 2014, 55(1):1232.
Salem, C. E., et al., "A preclinical study of prostate sentinel lymph node mapping with [99mTC]diethylenetetramine pentaacetic acid-mannosyl-dextran," J. Urol. 175: 2006, pp. 744-748.
Salmi, M., et al., "CD44 binds to macrophage mannose receptor on lymphatic endothelium and supports lymphocyte migration via afferent lymphatics," Circ. Res. 112: 2013, pp. 1577-1582.
Schlesinger, L. S., "Macrophage phagocytosis of virulent but not attenuated strains of *Mycobacterium tuberculosis* is mediated by mannose receptors in addition to complement receptors," J. Immunol. 150: 1993, pp. 2920-2930.
Shabo, I., et al., "Breast cancer expression of CD163, a macrophage scavenger receptor, is related to early distant recurrence and reduced patient survival," Int. J. Cancer 123: 2008, pp. 780-786.
Shabo, I., et al., "Expression of macrophage antigens by tumor cells," Adv. Exp. Med. Biol. 714: 2011, pp. 141-150.
Shi, S. R., et al., "Antigen retrieval in formalin-fixed, paraffin-embedded tissues: an enhancement method for immunohistochemical staining based on microwave oven heating of tissue sections," J. Histochem. Cytochem. 39: 1991, pp. 741-748.
Skobe, M., et al., "Induction of tumor lymphangiogenesis by VEGF-C promotes breast cancer metastasis," Nat. Med 7: 2001, pp. 192-198.
Sosabowski et al., "Conjugation of DOTA-like chelating agents to peptides and radiolabeling with trivalent metallic isotopes," Nature Protocols 1, 2006, pp. 972-976.
Stahl, P., et al., "Receptormediated pinocytosis of mannose glycoconjugates by macrophages: characterization and evidence for receptor recycling," Cell 19: 1980, pp. 207-215.
Tahara, N., et al., "2-deoxy-2-[18F]fluoro-D-mannose positron emission tomography imaging in atherosclerosis," Nat. Med. 20: 2014, pp. 215-219.
Taylor, P. R., et al., "Macrophage receptors and immune recognition," Annu. Rev. Immunol. 23: 2005, pp. 901-944.
Taylor, P. R., et al., "The mannose receptor: linking homeostasis and immunity through sugar recognition," Trends Immunol. 26: 2005, pp. 104-110.
Torrelles, J. B., et al., "Role of C-type lectins in mycobacterial infections," Curr. Drug Targets. 9: 2008, pp. 102-112 (Abstract provided).
Trubian et al., New Drug Approvals 2013—Pt. XII—Technetium Tc 99m Tilmanocept (LymphoSeek) [online]. The ChEMBL-og. Aug. 30, 2013 [retrieved on Nov. 30, 2015]. Retrieved from the Internet: <URL: http://chembl.blogspot.com/2013/08/new-drug-approvals-2013-ptxii.html>, 4 pages.
Uccini et al., "Kaposi's Sarcoma Cells Express the Macrophage-Associated Antigen Mannose Receptor and Develop in Peripheral Blood Cultures of Kaposi's Sarcoma Patients," AJP Merch 1997, 150: 929-938.
Vera, D. R., et al., "[(99m)Tc]MAG(3)-mannosyl-dextran: a receptor-binding radiopharmaceutical for sentinel node detection," Nucl. Med. Biol. 28: 2001, pp. 493-498.
Vera, D. R., et al., "A synthetic macromolecule for sentinel node detection: (99m)Tc-DTPA-mannosyl-dextran," J. Nucl. Med. 42: 2001, pp. 951-959.
Vera, D. R., et al., "Kinetic sensitivity of a receptor-binding radiopharmaceutical: technetium-99m galactosyl-neoglycoalbumin," J. Nucl. Med. 30: 1989, pp. 1519-1530.
Vera, D. R., et al., "Tc-99m galactosyl-neoglycoalbumin: in vitro characterization of receptor-mediated binding," J. Nucl. Med. 25: 1984, pp. 779-787.
Vera, D.R. et al., "Cy5.5-DTPA-galactosyl-dextran: a fluorescent probe for in vivo measurement of receptor biochemistry," Nuclear Medicine and Biology, 32 (2005) pp. 687-693.
Wallace, A. M., et al., Lymphoseek: a molecular imaging agent for melanoma sentinel lymph node mapping. Ann. Surg. Oncol. 14: 2007, pp. 913-921.
Wallace, A. M., et al., "Lymphoseek: a molecular radiopharmaceutical for sentinel node detection," Ann. Surg. Oncol. 10: 2003, pp. 531-538.
Wallace, A. M., et al., "Minimally invasive sentinel lymph node mapping of the pig colon with Lymphoseek," Surgery 139: 2006, pp. 217-223.
Wallace, A. M., et al., "Sentinel lymph node accumulation of Lymphoseek and Tc-99m-sulfur colloid using a '2-day' Protocol," Nucl. Med. Biol. 36: 2009, pp. 687-692.
Wang et al., "A novel delivery system of doxorubicin with high load and pH-responsive release from the nano particles of poly (alpha, beta-aspartic acid) derivative," European Journal of Pharmaceutical Sciences, 2012, vol. 47, pp. 256-264.
Wild, J., et al., "Isolation of mannose-binding proteins from human and rat liver," Biochem. J. 210: 1983, pp. 167-174.
Wileman, T., et al., "Monensin inhibits recycling of macrophage mannose-glycoprotein receptors and ligand delivery to lysosomes," Biochem. J. 220: 1984, pp. 665-675.
Wilting, J., et al., "The transcription factor Prox1 is a marker for lymphatic endothelial cells in normal and diseased human tissues," FASEB J 16: 2002, pp. 1271-1273.
Mm et al., "Synthesis of DOTA-Conjugated Multimeric [Tyr3] Octreotide Peptides via a Combination of Cu(I)-Catalyzed "Click" Cycloaddition and Thio Acid/Sulfonyl Azide "Sulfo-Click" Amidation and Their in Vivo Evaluation," 2010, J. Med. Chem., 53:3944-3953.
Yu, S.S., et al., "Macrophage-Specific RNA Interference Targeting via "Click", Mannosylated Polymeric Micelles," Mol. Pharm., 2013.
Dunford et al., "Structure-Activity Relationships Among the Nitrogen Containing Bisphosphonates in Clinical Use and Other Analogues: Time-Dependent Inhibition of Human Farnesyl Pyrophosphate Synthase" J. Med. Chem. 2008, 51, 2187-2195.
Camper et al., "Synthesis of an analogue of the bisphosphonate drug Ibandronate for targeted drug-delivery therapeutic strategies" New Journal of Chemistry, 2010.
Egorov et al., "A One-Pot Synthesis of 1-Hydroxy-1,1-bis(phosphonic acid)s Starting from the Corresponding Carboxylic Acids" Eur. J. Org. Chem. 2011, 7148-7154.
Fairweather et al., "Impact of α-modifications on the activity of triazole bisphosphonates as geranylgeranyl diphosphate synthase inhibitors" Bioorg. Med. Chem. 2021, vol. 44.

(56) References Cited

OTHER PUBLICATIONS

Hochdörffer et al., "Development of Novel Bisphosphonate Prodrugs of Doxorubicin for Targeting Bone Metastases That Are Cleaved pH Dependently or by Cathepsin B: Synthesis, Cleavage Properties, and Binding Properties to Hydroxyapatite As Well As Bone Matrix" J. Med. Chem. 2012, 55, 7502-7515.

Matsumoto et al., "Targeting Cancer Cells with a Bisphosphonate Prodrug" ChemMedChem 2016, 11, 1-9.

Plesselove et al., "Polyethylenimine-Bisphosphonate-Cyclodextrin Ternary Conjugates: Supramolecular Systems for the Delivery of Antineoplastic Drugs" J. Med. Chem. 2021, 64, 12245-12260.

\* cited by examiner

CD206 TARGETED DRUG DELIVERY VEHICLES CARRYING NOVEL BISPHOSPHONATE DRUG PAYLOADS VIA A DEGRADABLE LINKER

CROSS-REFERENCE TO RELATED APPLICATIONS

This application is a divisional of U.S. application Ser. No. 18/320,431, filed May 19, 2023, entitled "CD206 Targeted Drug Delivery Vehicles Carrying Novel Bisphosphonate Drug Payloads Via a Degradable Linker," which claims the benefit under 35 U.S.C. § 119(c) to U.S. Provisional Application No. 63/344,134, filed May 20, 2022, entitled "CD206 Targeted Drug Delivery Vehicles Carrying Novel Bisphosphonate Drug Payloads Via a Degradable Linker," and to U.S. Provisional Application No. 63/352,324, filed Jun. 15, 2022, entitled "CD206 Targeted Drug Delivery Vehicles Carrying Novel Bisphosphonate Drug Payloads Via a Degradable Linker," which are hereby incorporated by reference in their entirety for all purposes.

FIELD OF THE INVENTION

The disclosure relates to therapeutic constructs, methods of making, and methods of use thereof for releasing a therapeutic payload when internalized into a mannose-binding C-type lectin receptor-expressing cell, such as tumor associated macrophages (TAMs), and shifting the phenotype toward a proinflammatory state.

BACKGROUND OF THE INVENTION

Cancer is the second leading cause of death in the United States of America, accounting for nearly one of every four deaths. Cancer is characterized by the unregulated growth and cell division of cancer cells. However, cancers benefit enormously from chronic maladaptive immune responses to tumors, and macrophages are a key mediator of that maladaptive response. Macrophages are a common cell type in all tissues of the body and are important components of innate immunity. Macrophages also contribute significantly to the maintenance of tissue homeostasis and wound repair. In general, macrophages respond to various stimuli in their local microenvironment by altering their expression patterns for many, potentially hundreds, of genes. Such phenotypically altered macrophages are said to be activated macrophages. Depending upon which stimuli a macrophage is responding to, a wide range of activated phenotypic states can be attained. Among those genes that are differentially expressed upon macrophage activation are cell surface markers (such as, for example, the macrophage mannose receptor, CD206) and various cytokines, enzymatic pathways leading to the generation of reactive oxygen species (ROS), and other signaling molecules that can regulate the behavior of other components of the immune system, such as T lymphocytes (T-cells).

Extensive literature on macrophage activation have reported experimental results showing that there are a vast number of activated phenotypes and expression of only one or a few genes cannot accurately identify any one particular phenotype. However, these activated phenotypes can be characterized for their overall immune status and can be placed on a continuum, with highly pro-inflammatory phenotypes at one end of the continuum and immunosuppressive and wound healing phenotypes at the other end. Traditionally, as referenced by historic macrophage phenotype literature, activated macrophages were divided into two phenotypes: (1) classically activated, called M1, which is highly proinflammatory, and (2) alternatively activated, called M2, which is immunosuppressive and promotes wound healing. It is now understood that a strictly dichotomous classification of activated macrophage phenotypes is overly simplistic and does not represent the true plasticity of macrophage responses to stimuli from their microenvironments; however, the concept that activated macrophages can influence a local immune response by being either proinflammatory (M1-like) or immunosuppressive (M2-like) continues to have utility when describing the role of macrophages in various pathological states.

Tumor associated macrophages (TAMs) are abundant in tumors and highly significant contributors to the maladaptive immune response associated with cancer and other conditions. TAMs are the most numerous immune cells that infiltrate tumors and can comprise from about 5% to >30% of all cells in a tumor. While both M1-like and M2-like TAMs are known, the large majority of TAMs residing in or near established tumors are immunosuppressive, i.e., M2-like activated macrophages.

Bisphosphonate drugs have been given to cancer patients with metastases to the bones for many years. The structural components of bone are constantly being turned over in a process of continuous renewal in healthy individuals, with two cell types primarily involved in this bone turnover: (1) the osteoclasts, which degrade bone, and (2) the osteoblasts, which continuously lay down new bone. As osteoclasts are a type of macrophage, treatment with bisphosphonates may reduce the number of TAMs in bone metastases and, importantly, alter the phenotype of the remaining TAMs to be more M1-like. There is also some evidence that treatment with bisphosphonate drugs can slow the growth of bone metastases, which is postulated to be due to depriving the tumors of the pro-tumoral benefits and support provided by M2-like TAMs.

However, there are several challenges with using bisphosphonates as a TAM-targeted cancer immunotherapy: (1) inefficient cell penetration due to the highly charged nature of bisphosphonates preventing diffusion of these molecules across cellular lipid membranes; (2) rapid localization to bone; and (3) off-target toxicities. Historically, to overcome these limitations, liposomal constructs carrying various bisphosphonates were used to decrease bone localization and increase their payload delivery to TAMs. Some studies involving animal models of cancers utilized liposomal constructs that carried payloads of the bisphosphonate drug, clodronate. Clodronate is a non-nitrogenous bisphosphonate drug. Clodronate induces macrophages (including TAMs and osteoclasts) to undergo apoptosis, however, has a reduced ability to alter the phenotype of macrophages compared to nitrogenous bisphosphonates, such as zoledronic acid. Clodronate containing liposomes reduced the number of TAMs, however, have had limited tumor therapeutic potential.

More recent studies have evaluated liposomal constructs carrying payloads of zoledronic acid. Several of these studies evaluated targeted delivery of zoledronic acid to TAMs. At least two of these studies involved the attempted targeted delivery of zoledronic acid to TAMs. In one study, liposomes with zoledronic acid payloads were modified to display sialic acid on their exteriors. This modification targeted the liposomes to Siglecs (Sialic acid-binding immunoglobulin-type lectins) receptors on TAMs and other Siglecs expressing cells. This construct inhibited tumor growth in a mouse model. In another study, calcium/zoledronic acid nanoparticles were encapsulated in a modified lipid membrane displaying mannose and biotin. The mannose allowed binding to CD206 on TAMs, while the biotin allowed binding to biotin receptors on cancer cells. This dual targeted construct reduced tumor growth in the A549 mouse model of lung cancer; however, since the construct could kill both cancer cells and TAMs, it remains unclear whether the observed tumor growth reduction was due to the anti-tumor cell effects or to the TAM directed effects.

An additional problem with using liposomes or related constructs—either TAM targeted or not—with the intent to avoid bone localization and deliver bisphosphonates to TAMs, is that all liposomal constructs are relatively large compared to the mannosylated amine dextran (MAD) constructs described in this disclosure. The larger constructs provide challenges with regard to tumor penetration and localization to TAMs.

Accordingly, there remains a need for compositions and methods that induce the phenotypic change of the M2-like TAMs to M1-like TAMs in order to treat cancer with greater efficacy and lower toxicity.

Other objects, advantages and features of the present disclosure will become apparent from the following specification taken in conjunction with the accompanying figures.

BRIEF SUMMARY OF THE INVENTION

Provided herein are compounds and compositions containing a carbohydrate polymeric backbone and a bisphosphonate compound coupled thereto, and methods of making, and methods of using such compounds for the treatment of diseases.

In Example 1, a compound comprises a polymeric carbohydrate backbone, one or more mannose-binding C-type lectin receptor targeting moieties, and a nitrogenous bisphosphonate compound coupled to the polymeric carbohydrate backbone via a thiol-maleimide conjugation.

Example 2 relates to the compound of Example 1, wherein the compound comprises a subunit as shown in Formula (I):

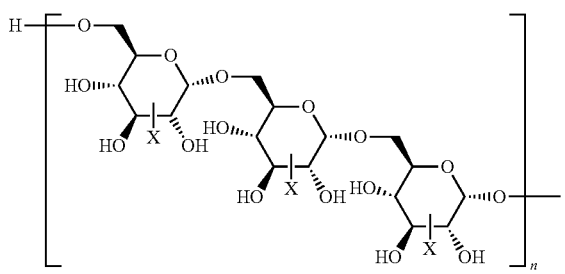

(I)

wherein
  each X is independently H, $L_1$-A-Z, or $L_2$-R, wherein each X is bound to an OH group;
  each of $L_1$ and $L_2$ are independently amine terminated leashes;
  each A independently comprises a substituted or unsubstituted maleimide moiety;
  each Z independently comprises a bisphosphonate compound modified with a hydrazone moiety or is absent;
  each R independently comprises the mannose-binding C-type lectin receptor targeting moiety or H; and n is an integer greater than zero, wherein each unit of n may be the same or different; and
  wherein at least one A is the substituted maleimide moiety and wherein the thiol-maleimide conjugation is between A and Z.

Example 3 relates to the compound of Example 2, wherein at least one X is $L_1$-A-Z, wherein at least one X is $L_2$-R, and wherein R comprises the mannose-binding C-type lectin receptor targeting moiety.

Example 4 relates to the compound of any one of Examples 1 to 3, wherein the polymeric carbohydrate backbone has a molecular weight between about 1 kD to about 50 kD.

Example 5 relates to the compound of any one of Examples 1 to 4, wherein the mannose-binding C-type lectin receptor targeting moiety comprises a mannosyl coupling aglycon moiety, mannose, high-mannose glycans or mannose oligosaccharides, fucose, N-acetylglucosamine, peptides, galactose, or a combination thereof.

Example 6 relates to the compound of any one of Examples 2 to 5, wherein at least one $L_1$ comprises —(CH$_2$)$_p$ S(CH$_2$)$_q$—NH—, wherein p and q are integers from 0 to 5.

Example 7 relates to the compound of any one of Examples 2 to 5, wherein at least one $L_2$ comprises —(CH$_2$)$_p$ S(CH$_2$)$_q$—NH—, wherein p and q are integers from 0 to 5.

Example 8 relates to the compound of any one of Examples 2 to 5, wherein the bisphosphonate compound is substituted with a carbonyl functional group prior to being modified to a hydrazone moiety.

Example 9 relates to the compound of any one of Examples 2 to 5, wherein the hydrazone moiety comprises an acyl hydrazone.

Example 10 relates to the compound of Example 9, wherein the hydrazone moiety has the following structure:

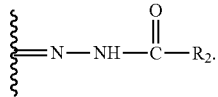

Example 11 relates to the compound of Example 10, wherein $R_2$ comprises —$R_4$—SH, wherein $R_4$ is a substituted or unsubstituted, linear or branched $C_1$-$C_{12}$ alkyl, alkenyl, alkynyl, or aromatic group.

Example 12 relates to the compound of Example 11, wherein $R_2$ comprises —(CH$_2$)$_2$SH.

In Example 13, a pharmaceutical composition comprises the compound according to any one of Examples 1 to 12, and a pharmaceutically acceptable carrier.

Example 14 relates to the composition of Example 13, wherein the compound comprises a subunit as shown in Formula (I):

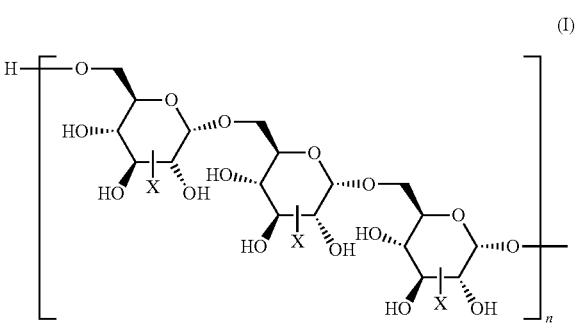

(I)

wherein
each X is independently H, $L_1$-A-Z, or $L_2$-R, wherein each X is bound to an OH group;

each of $L_1$ and $L_2$ are independently amine terminated leashes;

each A independently comprises a substituted or unsubstituted maleimide moiety;

each Z independently comprises a bisphosphonate compound modified with a hydrazone moiety or is absent;

each R independently comprises the mannose-binding C-type lectin receptor targeting moiety or H; and n is an integer greater than zero, wherein each unit of n may be the same or different; and wherein at least one A is the substituted maleimide moiety and wherein the thiol-maleimide conjugation is between A and Z.

In Example 15, a bisphosphonate compound according to Formula (II) is provided:

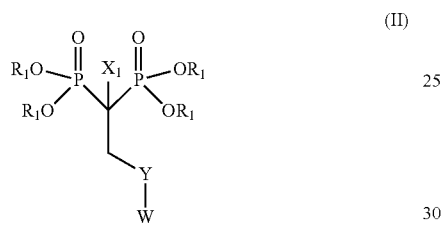

wherein
$R_1$ are each independently H, a positively-charged counter ion, a substituted or unsubstituted, linear or branched $C_1$-$C_6$ alkyl group, or an acyloxyalkyl group;

$X_1$ is either H, hydroxyl, a $C_1$-$C_6$ alkyl, or a O—$C_1$-$C_6$ alkyl group;

Y is absent, a $C_1$-$C_6$ alkyl group, or a heteroatom; and

W is a linear or branched $C_1$-$C_{12}$ alkyl, alkenyl, alkynyl, aromatic, or heteroaromatic group containing at least one nitrogen, wherein W is substituted with a carbonyl group.

Example 16 relates to the compound of Example 15, wherein W is the aromatic or heteroaromatic group, and wherein the aromatic or heteroaromatic group is selected from the group consisting of a phenyl, pyridine, pyrimidine, pyridazine, pyrazine, triazine, pyrazole, imidazole, triazole, tetrazole, thiazole, isothiazole, oxazole and isoxazole, or a pharmaceutically acceptable salt thereof.

Example 17 relates to the compound of Example 15 or 16, wherein W is further substituted with a $C_1$-$C_8$ alkyl group, an aromatic group, or a heteroaromatic group.

Example 18 relates to the compound of any one of Examples 15 to 17, wherein W is a thiazole, the carbonyl group is a ketone group, W is further substituted with a $C_1$ alkyl group, Y is NH, and $X_1$ is H.

Example 19 relates to the compound of any one of Examples 15 to 17, wherein W is an imidazole, the carbonyl group is a ketone group, Y is absent, and $X_1$ is a $C_1$ alkyl group.

Example 20 relates to the compound of any one of Examples 15 to 17, wherein the compound has the following formula (III):

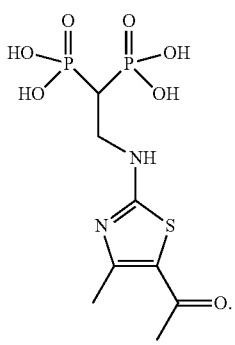

Example 21 relates to the compound of any one of Examples 15 to 17, wherein the compound has the following formula (IV):

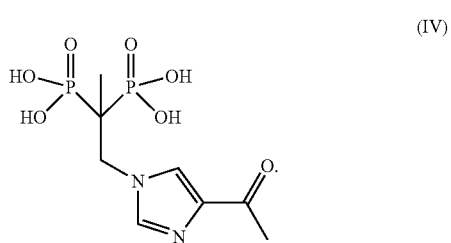 [SMILES: CC(=O)c1cn(CC(C)(P(=O)(O)O)P(=O)(O)O)cn1]

Example 22 relates to the compound of any one of Examples 15 to 21, wherein the carbonyl group is combined with an acylhydrazide to form a bisphosphonate compound modified with a hydrazone moiety.

Example 23 relates to the compound of Example 22, wherein the acylhydrazide has the following structure: $NH_2$—NH—C(O)—$R_2$.

Example 24 relates to the compound of Examples 22 or 23, wherein the hydrazone moiety has the following structure:

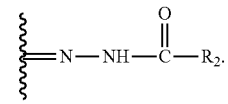

Example 25 relates to the compound of Example 23 or 24, wherein $R_2$ comprises —$R_4$—SH, wherein $R_4$ is a substituted or unsubstituted, linear or branched $C_1$-$C_{12}$ alkyl, alkenyl, alkynyl, or aromatic group.

Example 26 relates to the compound of Example 25, wherein $R_2$ comprises —$(CH_2)_2$SH.

Example 27 relates to the compound of Example 22, wherein the compound has the following formula (V):

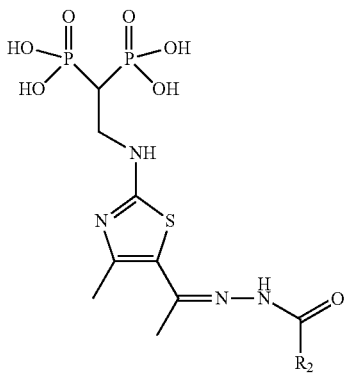

(V)

wherein $R_2$ comprises —$R_4$—SH, wherein $R_4$ is a substituted or unsubstituted, linear or branched $C_1$-$C_{12}$ alkyl, alkenyl, alkynyl, or aromatic group.

Example 28 relates to the compound according to Example 27, wherein $R_2$ comprises —$(CH_2)_2SH$.

Example 29 relates to the compound according to Example 22, wherein the compound has the following formula (VI):

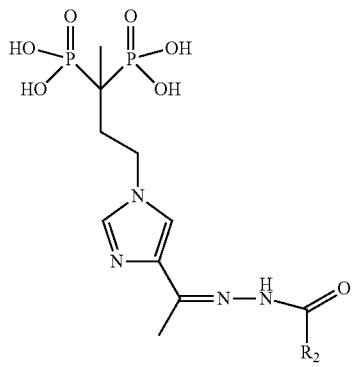

(VI)

wherein $R_2$ comprises —$R_4$—SH, wherein $R_4$ is a substituted or unsubstituted, linear or branched $C_1$-$C_{12}$ alkyl, alkenyl, alkynyl, or aromatic group.

Example 30 relates to the compound according to Example 29, wherein $R_2$ comprises —$(CH_2)_2SH$.

In Example 31, a method of making the compound according to Example 1 or 2 comprises (a) synthesizing a dextran backbone having one or more amine terminated leashes attached thereto; (b) synthesizing a nitrogenous bisphosphonate compound comprising a carbonyl functional group; (c) reacting the carbonyl functional group with an acylhydrazide to form the nitrogenous bisphosphonate compound modified with a hydrazone moiety; (d) modifying one or more amine terminated leashes with a maleimide moiety; and (e) substituting one or more maleimide moieties from step (d) with the bisphosphonate compound modified with the hydrazone moiety from step (c) through a thiol-maleimide conjugation.

Example 32 relates to the method according to Example 31, wherein step (d) may occur before step (b), after step (b), before step (c), or after step (c).

Example 33 relates to the method according to Example 31 or 32, wherein in Formula (I), at least one X is $L_1$-A-Z, wherein at least one X is $L_2$-R, and wherein R comprises the mannose-binding C-type lectin receptor targeting moiety.

Example 34 relates to the method according to any one of Examples 31 to 33, wherein the polymeric carbohydrate backbone has a molecular weight between about 1 kD to about 50 kD.

Example 35 relates to the method according to any one of Examples 31 to 34, wherein the mannose-binding C-type lectin receptor targeting moiety comprises a mannosyl coupling aglycon moiety, mannose, high-mannose glycans or mannose oligosaccharides, fucose, N-acetylglucosamine, peptides, galactose, or a combination thereof.

Example 36 relates to the method according to any one of Examples 31 to 35, wherein in Formula (I), at least one $L_1$ comprises —$(CH_2)_pS(CH_2)_q$—NH—, wherein p and q are integers from 0 to 5.

Example 37 relates to the method according to any one of Examples 31 to 35, wherein in Formula (I), at least one $L_2$ comprises —$(CH_2)_pS(CH_2)_q$—NH—, wherein p and q are integers from 0 to 5.

Example 38 relates to the method according to any one of Examples 31 to 37, wherein the hydrazone moiety has the following structure:

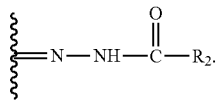

Example 39 relates to the method according to Example 38, wherein $R_2$ comprises —$R_4$—SH, wherein $R_4$ is a substituted or unsubstituted, linear or branched $C_1$-$C_{12}$ alkyl, alkenyl, alkynyl, or aromatic group.

Example 40 relates to the method according to Example 39, wherein $R_2$ comprises —$(CH_2)_2SH$.

In Example 41, a method of repolarizing a tumor associated macrophage (TAM) from an immunosuppressive (M2-like) phenotype to a proinflammatory (M1-like) phenotype comprises administering to a subject in need thereof an effective dose of a compound comprising a polymeric carbohydrate backbone, one or more mannose-binding C-type lectin receptor targeting moieties, and a bisphosphonate compound coupled to the polymeric carbohydrate backbone via a thiol-maleimide conjugation.

Example 42 relates to the method according to Example 41, wherein the compound comprises a subunit as provided in Formula (I):

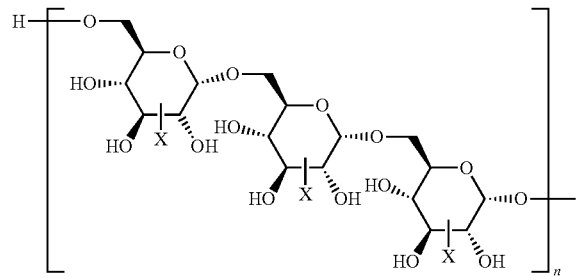

(I)

wherein
each X is independently H, $L_1$-A-Z, or $L_2$-R, wherein each X is bound to an OH group;

each of $L_1$ and $L_2$ are independently amine terminated leashes;

each A independently comprises a substituted or unsubstituted maleimide moiety;

each Z independently comprises a bisphosphonate compound modified with a hydrazone moiety or is absent;

each R independently comprises the mannose-binding C-type lectin receptor targeting moiety or H; and n is an integer greater than zero, wherein each unit of n may be the same or different; and wherein at least one A is the substituted maleimide moiety and wherein the thiol-maleimide conjugation is between A and Z.

Example 43 relates to the method according to Example 41 or 42, wherein the compound is administered in conjunction with at least one other therapy or treatment and, wherein the at least one other treatment or therapy is a chemotherapy, radiation therapy, or immunotherapy.

Example 44 relates to the method according to any one of Examples 41 to 43, wherein the bisphosphonate compound is released from the polymeric carbohydrate backbone at a pH of below about 5.5.

In Example 45, a method of treating a disease comprises administering to a subject in need thereof an effective amount of a compound according to any one of Examples 1 to 12, wherein the disease is cancer, an autoimmune disease, or an inflammatory disorder.

Example 46 is related to the method according to Example 45, wherein the compound is administered in conjunction with at least one other therapy or treatment and, wherein the at least one other treatment or therapy is a chemotherapy, radiation therapy, or immunotherapy.

Example 47 is related to the method according to Example 45 or 46, wherein the disease is cancer.

While multiple embodiments are disclosed, still other embodiments of the present disclosure will become apparent to those skilled in the art from the following detailed description, which shows and describes illustrative embodiments of the disclosure. Accordingly, the figures and detailed description are to be regarded as illustrative in nature and not restrictive.

Figure 1:
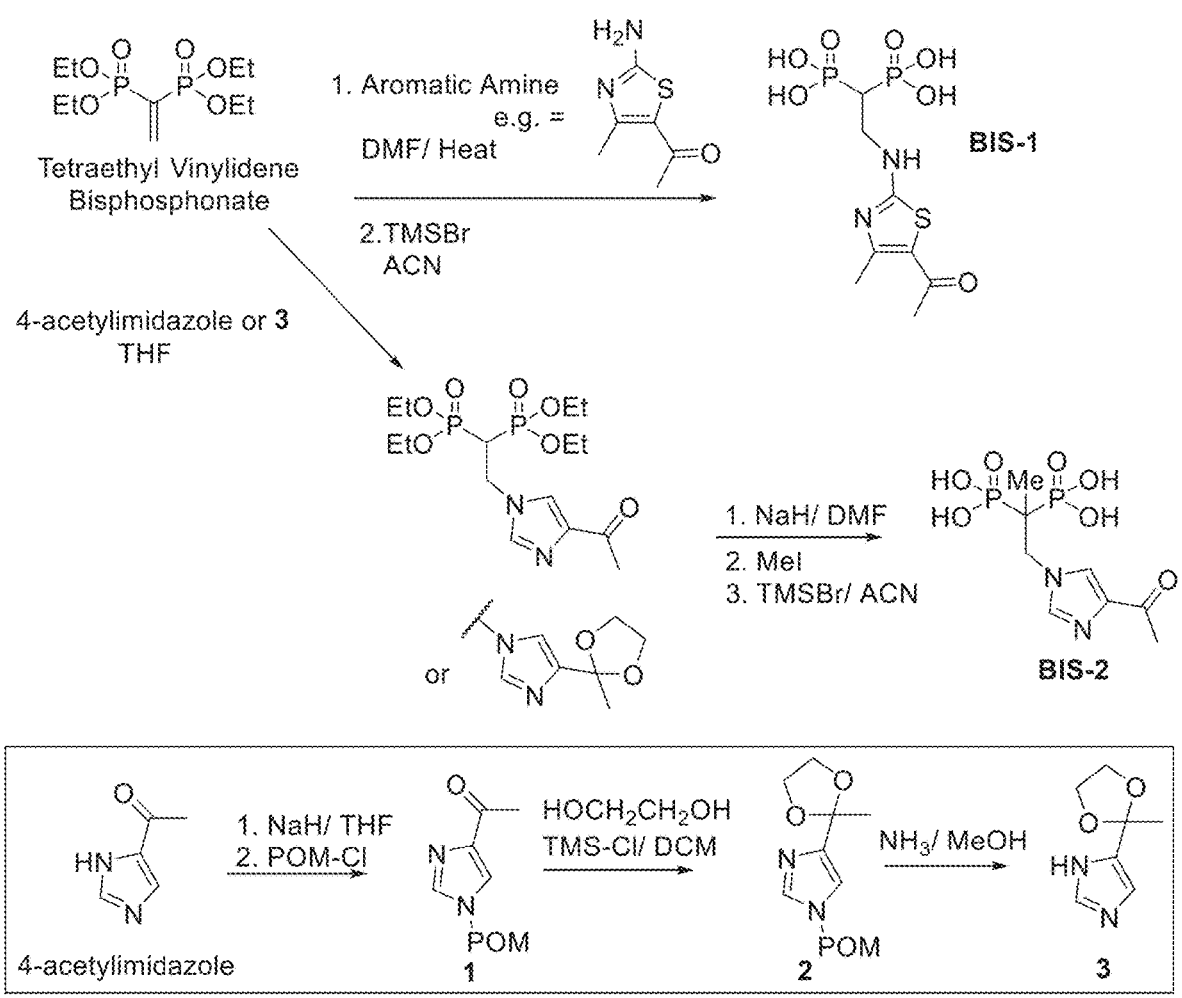
FIG. 1 shows the synthesis of BIS-1 and BIS-2 from tetraethyl vinylidene bisphosphonate and nitrogen heterocycles.

Various embodiments of the present disclosure will be described in detail with reference to the figures. Reference to various embodiments does not limit the scope of the disclosure. Figures represented herein are not limitations to the various embodiments according to the disclosure and are presented for exemplary illustration of the disclosure.

DETAILED DESCRIPTION

The embodiments of this disclosure are not limited to particular compounds, compositions, and methods, which can vary and are understood by skilled artisans. It is further to be understood that all terminology used herein is for the purpose of describing particular embodiments only and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾ This applies regardless of the breadth of the range.

So that the present disclosure may be more readily understood, certain terms are first defined. Unless defined otherwise, all technical and scientific terms used herein have the same meaning as commonly understood by one of ordinary skill in the art to which embodiments of the disclosure pertain. Many methods and materials similar, modified, or equivalent to those described herein can be used in the practice of the embodiments of the present disclosure without undue experimentation, the preferred materials and methods are described herein. In describing and claiming the embodiments of the present disclosure, the following terminology will be used in accordance with the definitions set out below.

The term "about," as used herein, refers to variation in the numerical quantity that can occur, for example, through typical measuring techniques and equipment, with respect to any quantifiable variable, including, but not limited to, mass, volume, and time. Further, given solid and liquid handling procedures used in the real world, there is certain inadvertent error and variation that is likely through differences in the manufacture, source, or purity of the ingredients used to make the compositions or carry out the methods and the like. The term "about" also encompasses these variations. Whether or not modified by the term "about," the claims include equivalents to the quantities.

The methods and compositions of the present disclosure may comprise, consist essentially of, or consist of the components and ingredients of the present disclosure as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

The term "actives" or "percent actives" or "percent by weight actives" or "actives concentration" are used interchangeably herein and refers to the concentration of those ingredients involved in cleaning expressed as a percentage minus inert ingredients such as water or salts. It is also sometimes indicated by a percentage in parentheses, for example, "chemical (10%)."

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. It is also contemplated that, in certain aspects, unless expressly indicated to the contrary, individual substituents can be further optionally substituted (i.e., further substituted or unsubstituted).

In defining various terms, "$A_1$," "$A_2$," "$A_3$," "$A_4$," "$X_1$," "$X_2$," "$Y_1$," "$Y_2$," etc. are used herein as generic symbols to represent various specific substituents. These symbols can be any substituent, not limited to those disclosed herein, and when they are defined to be certain substituents in one instance, they can, in another instance, be defined as some other substituents.

"$R_1$," "$R_2$," "$R_3$," "$R_n$," where n is an integer, as used herein can, independently, possess one or more of the groups listed above. For example, if RI is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group.

For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary.

Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

As used herein, the term "pharmaceutically acceptable carrier" or "carrier" refers to sterile aqueous or nonaqueous solutions, colloids, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

The term "polarization" is used herein to designate the phenotypic features and the functional features of the macrophages. The phenotype can be defined through the surface markers expressed by the macrophages. The functionality can be defined, for example, based on the nature and the quantity of chemokines and/or cytokines expressed, in particular, secreted by the macrophages. Indeed, the macrophages present different phenotypic and functional features depending of their state, either pro-inflammatory (M1-type) macrophage or anti-inflammatory (M2-type) macrophage. M2-type macrophages can be characterized by the expression of surface markers such as CD206, CD11b, PD-L1 and CD200R and then secretion of cytokines such as CCL17. M1-type macrophages can be defined by the expression of surface markers such as CD86 and CCR7 and the secretion of cytokines such as IL-6, TNF-a and IL12p40. In the context of the present disclosure, the term "repolarize" is used herein to refer to the induction of a change in phenotype of M1 macrophages population to M1-type macrophages.

As used herein, the term "cancer" refers to cells having the capacity for autonomous growth. Examples of such cells include cells having an abnormal state or condition characterized by rapidly proliferating cell growth. The term is meant to include cancerous growths, e.g., tumors; oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, cancer of the small intestine, and cancer of the esophagus. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knockout of a tumor suppressor gene, and cancer caused by infections, e.g., viral infections. The term "carcinoma" is art recognized and refers to malignancies of epithelial or endocrine tissues. In some embodiments, the present methods can be used to treat a subject having an epithelial cancer, e.g., a solid tumor of epithelial origin, e.g., lung, breast, ovarian, prostate, renal, pancreatic, or colon cancer.

As used herein, the term "subject" refers to the target of administration, e.g., an animal. Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more cancer disorders prior to the administering step.

As used herein, the term "synergistic" means that the effect achieved with the methods and combinations of this invention is greater than the sum of the effects that result from using the compounds, compositions, treatments and/or methods a pharmaceutically acceptable salt thereof, separately. Advantageously, such synergy provides greater efficacy at the same doses, and/or prevents or delays the build-up of multi-drug resistance.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with cancer" means having been subjected to a physical examination by a person of skill, for example, a physician, and found to have a condition that can be diagnosed or treated by a compound or composition that can reduce tumor size or slow rate of tumor growth. A subject having cancer, tumor, or at least one cancer or tumor cell, may be identified using methods known in the art. For example, the anatomical position, gross size, and/or cellular composition of cancer cells or a tumor may be determined using contrast-enhanced MRI or CT. Additional methods for identifying cancer cells can include, but are not limited to, ultrasound, bone scan, surgical biopsy, and biological markers (e.g., serum protein levels and gene expression profiles). An imaging solution comprising a cell-sensitizing composition of the present invention may be used in combination with MRI or CT, for example, to identify cancer cells.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, administration to specific organs through invasion, intramuscular administration, intratumoral administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

Effective dosages may be estimated initially from in vitro assays. For example, an initial dosage for use in animals may be formulated to achieve a circulating blood or serum concentration of active compound that is at or above an $IC_{50}$ of the particular compound as measured in an in vitro assay. Calculating dosages to achieve such circulating blood or serum concentrations, taking into account the bioavailability of the particular active agent, is well within the capabilities of skilled artisans. For guidance, the reader is referred to Fingl & Woodbury, "General Principles," In: Goodman and Gilman's The Pharmaceutical Basis of Therapeutics, Chapter 1, pp. 1-46, latest edition, Pergamagon Press, which is hereby incorporated by reference in its entirety, and the references cited therein.

The phrase "anti-cancer composition" can include compositions that exert antineoplastic, chemotherapeutic, anti-viral, antimitotic, antitumorgenic, anti-angiogenic, anti-metastatic and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agents available in commercial use, in clinical evaluation and in pre-clinical development, which could be included in this application by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophyllotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and vinca alkaloids. The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

The term "weight percent," "wt. %," "wt-%," "percent by weight," "% by weight," and variations thereof, as used herein, refer to the concentration of a substance as the weight of that substance divided by the total weight of the composition and multiplied by 100.

The present disclosure describes compounds, compositions, and methods with utility for altering or transitioning the phenotype of activated macrophages from being an immunosuppressive phenotype to a proinflammatory phenotype (referred to herein as "repolarizing"). The ability to alter or transition the phenotype of activated macrophages from immunosuppressive to proinflammatory constitutes a therapeutic modality for cancer, various infectious diseases and other medical conditions. The present disclosure further describes a drug delivery vehicle and methods of use that enables the targeted delivery of bisphosphonates and related therapeutic agents to TAMs with the intent to repolarize the TAMs. TAM-targeted delivery provides higher mass doses of the bisphosphonates and related therapeutic agents to TAMs—increasing phenotype altering effects—while limiting potentially toxic exposure to off target cells and tissues. Through the use of the disclosed compounds, compositions and methods, M2-like (immunosuppressive) activated macrophages can be induced to switch their phenotype to a M1-like (proinflammatory) activated phenotype.

Compounds and Compositions

In certain aspects, compounds disclosed herein employ a carrier construct comprising a polymeric carbohydrate backbone having conjugated thereto mannose-binding C-type lectin receptor targeting moieties (e.g. mannose, fucose, N-acetylglucosamine) to deliver one or more active therapeutic agents. Examples of such constructs include mannosylated amine dextrans (MADs), which comprise a dextran backbone having mannose molecules conjugated to glucose residues of the backbone and having an active pharmaceutical ingredient conjugated to glucose residues of the backbone. Tilmanocept is a specific example of a MAD. A tilmanocept derivative that is tilmanocept without DTPA conjugated thereto is a further example of a MAD.

MADs are synthetic molecules purposefully designed to be high affinity ligands for mannose-binding C-lectin type receptors, such as, for example, CD206. MADs have been described in U.S. Pat. No. 6,409,990, which is hereby incorporated by reference in its entirety. Thus, the backbone comprises a plurality of glucose moieties (i.e., residues or subunits) primarily linked by $\alpha$-1,6 glycosidic bonds. Other linkages such as $\alpha$-1,4 and/or $\alpha$-1,3 bonds may also be present. In some embodiments, not every backbone moiety is substituted. In some embodiments, one or more amine terminated leashes are attached to the backbone. In further embodiments, mannose-binding C-type lectin receptor targeting moieties are attached to the one or more amine terminated leashes. In certain embodiments, the mannose-binding C-type lectin targeting moieties are attached to between about 15% and about 70%, between about 17% and about 65%, or about 20% and about 60% of the glucose residues via the amine terminated leashes. In further embodiments, the mannose-binding C-type lectin targeting moieties are attached to up to about 60%, up to about 70%, up to about 80%, up to about 90%, or up to about 100% of the glucose residues via the amine terminated leashes. In certain aspects, the percentages may vary depending on the size of the dextran backbone. In even further embodiments, one or more therapeutic agents are attached to the glucose residues via the amine terminated leashes, as well as a hydrazone linker, which is linked to the backbone using a thiol-maleimide conjugation, as described in greater detail below. In certain embodiments, the therapeutic agents are attached to between about 1% and about 25%, between about 2% and about 20%, or about 5% and about 15% of the glucose residues via the amine terminated leash and hydrazone linker, linked via a thiol-maleimide conjugation, as described herein.

The size of a MAD can be varied by changing the size of the initial dextran upon which the MAD construct is assembled. In some embodiments, the dextran-based moiety is about 50-100 kD. The dextran-based moiety may be at least about 50 kD, at least about 60 kD, at least about 70 kD, at least about 80 kD, or at least about 90 kD. The dextran-based moiety may be less than about 100 kD, less than about 90 kD, less than about 80 kD, less than about 70 kD, or less than about 60 kD. Alternatively, in some embodiments, the dextran backbone has a MW of between about 1 kD and about 50 kDa, while in other embodiments the dextran backbone has a MW of between about 5 kD and about 25 kDa. In still other embodiments, the dextran backbone has a MW of between about 8 kD and about 15 kDa, such as about 10 kDa. While in other embodiments, the dextran backbone has a MW of between about 1 kDa and about 5 kDa, such as about 3 kDa. As described in Bartels et al (Mol Imaging Biol. 2023 Mar. 7. doi: 10.1007/s11307-023-01809-6. Online ahead of print), MAD-based constructs with initial dextrans upon which they were constructed or assembled and varying in size between 3.5 kDa to 150 kDa all bind avidly to CD206.

In contrast to larger liposomal constructs, which may be about 84 nm or larger in diameter, the molecular weights of the disclosed MAD constructs may, in some aspects, have diameters of from about 15 nm or less, about 12 nm or less, about 10 nm or less, about 7 nm or less, or about 5 nm or less. Beneficially, the smaller sizes of the disclosed constructs enable greater tumor penetration and greater localization to TAMs than is possible with previously used liposome constructs.

According to certain embodiments, and as further described throughout the disclosure, one or more mannose-binding C-type lectin receptor targeting moieties and one or more therapeutic agents are each independently attached to the dextran-based backbone by way of a leash. As described in greater detail below, one or more additional moieties may be present between the leash and the mannose-binding C-type lectin receptor targeting moieties or the therapeutic agent. In further embodiments, the leash is not attached to a mannose-binding C-type lectin receptor targeting moiety or a therapeutic agent, and instead, is provided as a standalone leash attached to the dextran-based backbone. The leash may be attached to from about 50% to about 100% of the backbone moieties, or from about 70% to about 90% of the backbone moieties. The leashes may be the same or different. In some embodiments, the leash is an amine terminated leash. In some embodiments, the leashes may comprise the formula —(CH$_2$)$_p$S(CH$_2$)$_q$—NH—, wherein p and q are integers from 0 to 5. In further embodiments, the leash comprises the formula —(CH$_2$)$_3$S(CH$_2$)$_2$NH—. In embodiments where the leash is not attached to a mannose-binding C-type lectin receptor targeting moiety or a therapeutic agent, the leash may comprise the formula —(CH$_2$)$_p$S(CH$_2$)$_q$—NH$_2$, wherein p and q are integers from 0 to 5.

In some embodiments, the leash may be a chain of from about 1 to about 20 member atoms selected from carbon, oxygen, sulfur, nitrogen and phosphorus. The leash may be a straight chain or branched. The leash may also be substituted with one or more substituents including, but not limited to, halo groups, perfluoroalkyl groups, perfluoroalkoxy groups, alkyl groups, such C$_{1-4}$ alkyl, alkenyl groups, such as C$_{1-4}$ alkenyl, alkynyl groups, such as C$_{1-4}$ alkynyl, hydroxy groups, oxo groups, mercapto groups, alkylthio groups, alkoxy groups, nitro groups, azidealkyl groups, aryl or heteroaryl groups, aryloxy or heteroaryloxy groups, aralkyl or heteroaralkyl groups, aralkoxy or heteroaralkoxy groups, HO—(C=O)— groups, heterocylic groups, cycloalkyl groups, amino groups, alkyl- and dialkylamino groups, carbamoyl groups, alkylcarbonyl groups, alkylcarbonyloxy groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups, —NH—NH$_2$; =N—H; =N-alkyl; —SH; —S-alkyl; —NH—C(O)—; —NH—C(=N)— and the like. As would be apparent to one skilled in the art, other suitable leashes are possible. In other embodiments, the mannose-binding C-type lectin targeting moieties may be conjugated to the amine group of the amine terminated leash via an amidine and/or amide linker.

According to certain embodiments, the MAD constructs disclosed herein contain at least one mannose-binding C-type lectin receptor targeting moiety. In further embodiments, the MAD constructs disclosed herein contain at least one targeting ligand. CD206 is a C-type lectin receptor expressed on macrophages, dendritic cells, and mesangial cells. CD206 binds to molecules that display multiple terminal mannose moieties. Without being limited to any particular mechanism or theory, once CD206 binds to a ligand, the receptor/ligand complex is internalized by receptor mediated endocytosis to endosomes that become naturally acidified to a pH of 4-5.5. At this lower pH, CD206 releases its ligand and recycles to the cell surface. In some aspects, the inclusion of the mannose-binding C-type lectin receptor targeting moiety within the MAD construct provides numerous benefits in delivering a therapeutic agent to a target, such as macrophages. According to some embodiments, the mannose-binding C-type lectin receptor targeting moiety comprises mannose, high-mannose glycans or mannose oligosaccharides, fucose, or N-acetylglucosamine, peptides, or galactose. In further embodiments, the mannose-binding C-type lectin receptor targeting moiety is attached to the amine terminated leash via an electrophilic imidate appended to mannose (may also be referred to herein as "mannosyl coupling aglycon moiety") as described in U.S. Pat. No. 6,409,990, which is hereby incorporated by reference in its entirety. As such, in some embodiments, the mannose-binding C-type lectin receptor targeting moiety comprises the mannosyl coupling aglycon moiety, mannose, high-mannose glycans or mannose oligosaccharides, fucose, N-acetylglucosamine, peptides, galactose or a combination thereof. In further embodiments, the mannose-binding C-type lectin receptor targeting moiety comprises mannose. In other embodiments, the at least one targeting ligand may be sialic acid.

According to some embodiments, the MAD constructs described herein may optionally contain a maleimide moiety. In some aspects, the maleimide moiety is attached to the carbohydrate-based backbone via a leash as described herein. In further aspects, the leash is an amine-terminated leash. The maleimide moiety may comprise any compound containing a maleimide. In some embodiments, the maleimide moiety is terminated with the maleimide group. In embodiments, the maleimide moiety comprises a C$_{1-12}$ alkyl chain, wherein one or more carbon atoms may be substituted with an O, S, or N. In some embodiments, the terminal maleimide group within the maleimide moiety may be substituted or unsubstituted. In some aspects, the unsubstituted maleimide moiety may comprises the formula —C(O)(CH$_2$)$_2$[H$_2$C$_2$(CO)$_2$N]. In further aspects, the maleimide moiety may be substituted. In some embodiments, the substituted maleimide moiety may have the formula —C(O)(CH$_2$)$_2$[H$_3$C$_2$(CO)$_2$N]—. In some embodiments, where the maleimide moiety is substituted, the maleimide moiety is substituted with a compound having a terminal thiol group, thereby forming a thiol-maleimide conjugation. According to certain embodiments, and discussed in further detail below, a therapeutic agent may be attached to the maleimide moiety via a thiol-maleimide conjugation.

In some embodiments, one or more therapeutic agents are attached to the MAD construct. In certain embodiments, the therapeutic agent is a bisphosphonate. Suitable bisphosphonates include nitrogenous bisphosphonates. Bisphosphonates bind to calcium and, as a result, accumulate in bone. Bone is a complex organ with many functions, where the structural components of bone are constantly being turned over in a process of continuous renewal in healthy individuals. There are two cell types primarily involved in this bone turnover: (1) the osteoclasts degrade bone, and (2) the osteoblasts continuously lay down new bone. Strong, healthy bone is maintained as a dynamic equilibrium between the actions of osteoclasts and osteoblasts. In pathological conditions, such as osteoporosis or metastatic cancer of the bone, this equilibrium is disrupted such that bone is degraded faster than it is replaced, resulting in weak and easily fractured bones. In patients administered bisphosphonate drugs, osteoclasts ingest the drugs when they degrade bone. As a result, the osteoclasts that have ingested bisphosphonates change their phenotype to degrade bone less efficiently or are induced to kill themselves by apoptosis. With the activity of osteoclasts thereby diminished, the osteoblasts can lay down new bone faster than it is being degraded, resulting in stronger bones that resist fracture. Bisphosphonate drugs have been used to successfully treat patients with osteoporosis for decades. Bisphosphonate treatment reduces metastases related bone pain and reduces the rate of metastases related bone fractures.

Without being limited to any particular theory or mechanism, bisphosphonates may be able to address two TAM-targeted cancer therapeutic strategies, including, killing or ablating TAMs, and causing TAMs to switch their phenotypes from M2-like to M1-like. This makes bisphosphonates suitable therapeutic agents for the compositions and methods disclosed herein.

Bisphosphonates are a class of drugs that have the generalized structure as shown below.

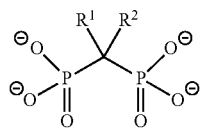

In this structure, there are two phosphonate groups attached to a central carbon atom. To the other two potential bonds of the central carbon, various other chemical moieties can be attached, shown as $R^1$ and $R^2$ groups. $R^1$ and $R^2$ can be different chemical moieties and can range in complexity from simple hydrogen atoms (H), chlorine (Cl) atoms, or hydroxyl (OH) groups, to more complex organic structures. In many current commercially available pharmaceutical bisphosphonate drugs, one of the R groups is a complex organic molecule that includes one or more nitrogen atoms. The nitrogenous (nitrogen containing) bisphosphonate drugs tend to be more pharmacologically active than the non-nitrogenous bisphosphonate drugs. In some aspects, one of the most pharmacologically active FDA approved bisphosphonate drugs is the nitrogenous bisphosphonate, zoledronic acid (zoledronate). In embodiments, the present disclosure provides for novel bisphosphonate drugs that contain a chemical moiety not found in zoledronic acid that permits them to be attached to the MAD constructs via degradable linkers described in further detail herein.

In embodiments, a compound is provided comprising a polymeric carbohydrate backbone, one or more mannose-binding C-type lectin receptor targeting moieties, and a bisphosphonate compound coupled to the polymeric carbohydrate backbone via a thiol-maleimide conjugation as described herein. In some embodiments, the compound may comprise a subunit as shown in Formula (I):

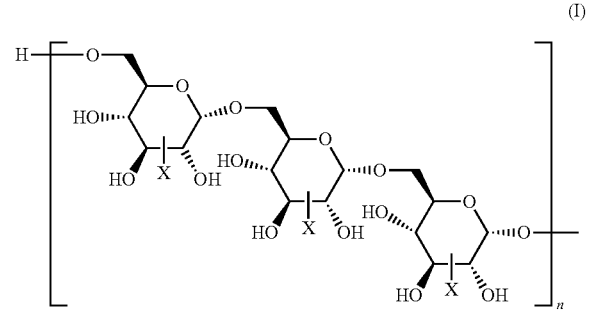

wherein each X is independently H, $L_1$-A-Z, or $L_2$-R, wherein each X is bound to an OH group;

each of $L_1$ and $L_2$ are independently amine terminated leashes;

each A independently comprises a substituted or unsubstituted maleimide moiety;

each Z independently comprises a bisphosphonate compound modified with a hydrazone moiety or is absent;

each R independently comprises the mannose-binding C-type lectin receptor targeting moiety or H; and n is an integer greater than zero, wherein each unit of n may be the same or different.

In embodiments, at least one A is the substituted maleimide moiety, wherein the thiol-maleimide conjugation is between A and Z.

In further embodiments, at least one X is $L_1$-A-Z. In further aspects, at least one X is $L_2$-R, wherein R comprises the mannose-binding C-type lectin receptor targeting moiety. As described herein, the mannose-binding C-type lectin receptor targeting moiety may comprise a mannosyl coupling aglycon moiety, mannose, high-mannose glycans or mannose oligosaccharides, fucose, N-acetylglucosamine, peptides, galactose, or a combination thereof.

As described within the present disclosure, the substituted maleimide moiety and/or the mannose-binding C-type lectin receptor targeting moiety may be attached to the polymeric backbone by way of a leash. The leash may be any leash as described throughout the disclosure. In embodiments, at least one $L_1$ comprises $-(CH_2)_pS(CH_2)_q-NH-$, wherein p and q are integers from 0 to 5. In further embodiments, at least one $L_2$ comprises $-(CH_2)_pS(CH_2)_q-NH-$, wherein p and q are integers from 0 to 5.

In some aspects, n is an integer greater than zero. In other aspects, n is an integer greater than 1. In further aspects, n may be an integer between 1 and about 50, between about 5 and about 40, or between about 5 and about 30. As would be understood by those skilled in the art, each unit of n may be the same or may be different. As each X may independently be H, $L_1$-A-Z, or $L_2$-R, each unit of n may consist of any combination of X selected from H, $L_1$-A-Z, or $L_2$-R.

Bisphosphonate compounds suitable for coupling to the polymeric carbohydrate backbone via the thiol-maleimide conjugation are further provided below. In some embodiments, the bisphosphonate compound itself is provided. In an aspect, the bisphosphonate compound may comprise a compound according to Formula (II):

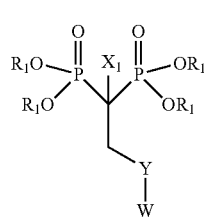

(II)

wherein
- $R_1$ are each independently H, a positively-charged counter ion, a substituted or unsubstituted, linear or branched $C_1$-$C_6$ alkyl group, or an acyloxyalkyl group;
- $X_1$ is either H, hydroxyl, a $C_1$-$C_6$ alkyl, or an O—$C_1$-$C_6$ alkyl group;
- Y is absent, a $C_1$-$C_6$ alkyl group, or a heteroatom; and
- W is an unsubstituted or substituted, linear or branched $C_1$-$C_{12}$ alkyl, alkenyl, alkynyl, aromatic, or heteroaromatic group.

In certain implementations, the positively-charged counter ion may include, but is not limited to, an alkali metal, an alkaline earth metal, quaternary amine or ammonium, or any other positively-charged counter ion. For example, the positively-charged counter ion may include sodium, potassium, lithium, rubidium, caesium, francium, calcium, magnesium, barium, beryllium, strontium, or radium. In further examples, the positively-charged ion may include sodium, potassium, lithium, calcium, or magnesium. As would be understood by those having ordinary skill in the art, additional positively-charged counter ions may further be considered.

In some implementations, the acyloxyalkyl group may include, but is not limited to, pivaloyloxymethyl (POM), ethoxycarbonyloxyethyl, or acetoxymethyl (AM). In some embodiments, the acyloxyalkyl group may comprise pivaloyloxymethyl.

In certain implementations, W is a substituted, linear or branched $C_1$-$C_{12}$ alkyl, alkenyl, alkynyl, aromatic or heteroaromatic group containing at least one nitrogen, wherein W is substituted with a carbonyl group. In some embodiments, the carbonyl group is selected from the group consisting of an aldehyde, ketone, and enone. In further embodiments, the carbonyl group is a ketone. In some embodiments, W is further substituted with a $C_1$-$C_8$ alkyl group, a halogen, an aromatic, or a heteroaromatic group.

In certain implementations, W is the aromatic or heteroaromatic group. In some embodiments, the aromatic or heteroaromatic group is selected from the group consisting of a phenyl, pyridine, pyrimidine, pyridazine, pyrazine, triazine, pyrazole, imidazole, triazole, tetrazole, thiazole, isothiazole, oxazole and isoxazole, or a pharmaceutically acceptable salt thereof. In some embodiments, the aromatic or heteroaromatic group is the thiazole or imidazole.

In some embodiments, W is a thiazole, the carbonyl group is a ketone group, W is further substituted with a $C_1$ alkyl group, Y is NH, and $X_1$ is H. In further embodiments, W is an imidazole, the carbonyl group is a ketone group, Y is absent, and $X_1$ is a $C_1$ alkyl group.

In certain embodiments, the bisphosphonate compound may have the following Formula (III):

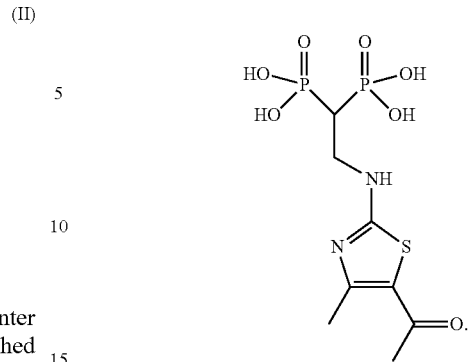

(III)

In other embodiments, the bisphosphonate compound may have the following Formula (IV):

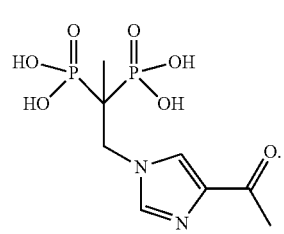

(IV)

In certain implementations, the bisphosphonate compound of Formula (II) is provided wherein W is substituted with a carbonyl group. In further aspects, the carbonyl group is combined with an acylhydrazide to form a bisphosphonate compound modified with a hydrazone moiety. In some embodiments, the acylhydrazide has the following structure: $NH_2$—NH—C(O)—$R_2$. In certain embodiments, $R_2$ comprises —$R_4$—SH, wherein $R_4$ is a substituted or unsubstituted, linear or branched $C_1$-$C_{12}$ alkyl, alkenyl, alkynyl, or aromatic group. In exemplary embodiments, $R_2$ comprises —$(CH_2)_2$SH. Beneficially, in some implementations, the hydrazone moiety contains a terminal thiol group. In aspects, when the acylhydrazide is combined with the carbonyl group of Formula (II), a bisphosphonate compound modified with a hydrazone moiety is formed. In these implementations, the hydrazone moiety has the following structure:

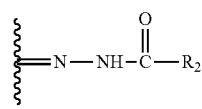

wherein $R_2$ comprises the —$R_4$—SH of the acylhydrazide. In embodiments, the bisphosphonate compound modified with a hydrazone moiety has the following Formula (V):

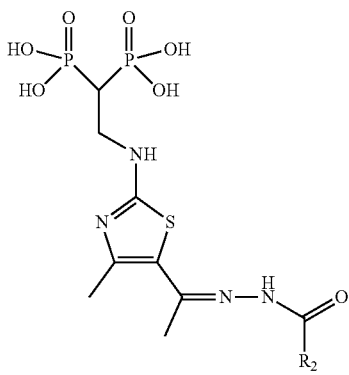

(V)

wherein R₂ comprises —R₄—SH, wherein R₄ is a substituted or unsubstituted, linear or branched $C_1$-$C_{12}$ alkyl, alkenyl, alkynyl, or aromatic group. In exemplary embodiments, R₂ comprises —(CH₂)₂SH.

In other embodiments, the bisphosphonate compound modified with a hydrazone moiety has the following Formula (VI):

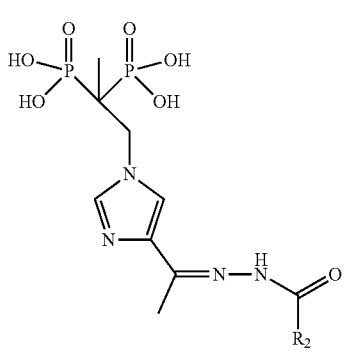

(VI)

wherein R₂ comprises —R₄—SH, wherein R₄ is a substituted or unsubstituted, linear or branched $C_1$-$C_{12}$ alkyl, alkenyl, alkynyl, or aromatic group. In exemplary embodiments, R₂ comprises —(CH₂)₂SH.

In further embodiments, the bisphosphonate compounds disclosed herein may be attached to the MAD constructs disclosed. In some aspects, the bisphosphonate compounds are modified with a hydrazone moiety prior to being attached to the dextran-based backbone. In further aspects, the bisphosphonate compound is substituted with a carbonyl functional group prior to being modified to the hydrazone moiety. In certain embodiments where the bisphosphonate compounds modified with a hydrazone moiety are to be attached to the MAD construct, the dextran-based backbone already comprises one or more leashes attached to a maleimide moiety as disclosed herein. In certain aspects, the hydrazone moiety of the bisphosphonate compound comprises a terminal thiol group. This terminal thiol group allows for the attachment of the bisphosphonate compound to the dextran-based backbone via a thiol-maleimide conjugation. In certain implementations, the thiol group of the hydrazone moiety is conjugated to the maleimide group of the maleimide moiety. In embodiments, the hydrazone moiety comprises an acyl hydrazone. Without being limited to any particular theory or mechanism, at neutral pH, the constructs retain their payloads (such as a drug payload comprising the therapeutic agent) long enough to carry them into an endosome, and once the construct is inside an acidified endosome, the drug payload is released.

According to certain embodiments, the disclosed compounds can include a pharmaceutically acceptable carrier and a compound or a pharmaceutically acceptable salt of the compounds disclosed herein. The disclosed compounds, or pharmaceutically acceptable salts thereof, can also be included in pharmaceutical compositions in combination with one or more other therapeutically active compounds. In embodiments, the pharmaceutically acceptable carrier employed may be, for example, a solid, liquid, or gas. Examples of solid carriers include lactose, mannitol, microcrystalline cellulose, terra alba, sucrose, talc, gelatin, agar, pectin, acacia, magnesium stearate, and stearic acid. Examples of liquid carriers are sugar syrup, peanut oil, olive oil, ethanol, propylene glycol, and water. Examples of gaseous carriers include carbon dioxide, nitrogen, and compressed air.

In preparing the compositions into a dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their case of administration, tablets and capsules are the preferred oral dosage units whereby solid pharmaceutical carriers are employed. Optionally, tablets can be coated by standard aqueous or nonaqueous techniques. In further aspects, aerosol carriers such as sugars comprising glucose, fructose, mannitol, sucrose, lactose, and cellulose, propellants, liquid carriers, and gaseous carriers may be utilized to form preparations suitable for inhalation. In certain aspects, the compositions are administered intravenously, intraperitoneally, intramuscularly, orally, subcutaneously, intra-tumorally or transdermally. In preferred embodiments, the compositions are administered intravenously.

In certain aspects, the compound is administered in a therapeutically effective amount. In further aspects, the compound is administered in a prophylactically effective amount.

Molecular weights referenced herein, as well as the number and degree of conjugation of receptor substrates, leashes, and therapeutic moieties attached to the dextran backbone refer to average amounts for a given quantity of carrier molecules, since the synthesis techniques will result in some variability.

Methods

In living humans and animals, activated macrophages have been observed that have a mixed activated phenotype with features of both M1-like and M2-like phenotypic states. Examples of stimuli that can induce an M1-like phenotype in macrophages include tumor necrosis factor (TNF), interferon gamma (INFγ), and toll-like receptor (TLR) agonists such as lipopolysaccharide (LPS). Examples of stimuli that can induce an M2-like phenotype in macrophages include interleukin 4 (IL4), interleukin 13 (IL13), and tumor growth factor beta (TGFβ). There are many other hormones, cytokines, chemokines, and environmental factors that can also affect macrophage phenotypes.

Examples of cell surface markers and secreted proteins that frequently have altered levels of expression in M1-like and M2-like activated macrophages are shown in Table 1. In addition, two immune checkpoint receptors, PD-1 and SIRPα, can be expressed on the surface of macrophages. When these immune checkpoint receptors bind to their ligands, PD-L1 and CD47 respectively, a signal is generated that represses a macrophage's phagocytic activity. An M1-like macrophage would be expected to attack and phagocytize perceived pathogens or tumor cells. However, if the M1-like macrophage was expressing PD-1 and/or SIRPα that had bound to its ligand, phagocytosis would be repressed.

TABLE 1

Examples of Proteins that Increase in Expression in Activated Macrophages with M1-Like and M2-Like Phenotypes

| Increased in M1-like | | Increased in M2-like | |
|---|---|---|---|
| Cell Surface | Secreted | Cell Surface | Secreted |
| MHC II | TNF | CD163 | IL-10 |
| CD80 | IL-1 | CD206 | IL-13 |
| CD86 | IL-12 | | TGFβ |

Under the influence of the M2-like TAMs, the tumor immune microenvironment becomes tumor promoting and immunosuppressive, repressing the anti-tumor activity of other immune cells such as lymphocytes. The tumor promoting and immunosuppressive activities of M2-like TAMs reduce the efficacies of anti-cancer therapies and, perhaps most notably, of anti-cancer immunotherapies. For these reasons, TAMs are an important therapeutic target for cancer. TAM targeted cancer therapeutic strategies include: (1) killing or ablating TAMs; (2) blocking recruitment of TAMs to tumors; or (3) causing TAMs to switch their phenotypes from M2-like to M1-like. This third strategy is sometimes referred to as TAM repolarization or TAM reeducation. M1-like TAMs will attack tumor cells and stimulate other types of immune cells, such as lymphocytes, to do the same.

In certain embodiments, a method of repolarizing a TAM from an immunosuppressive (M2-like) phenotype to a proinflammatory (M1-like) phenotype is disclosed. In certain aspects, the MAD constructs carrying a therapeutic agent, such as the disclosed bisphosphonate compounds, are appended via a pH sensitive hydrazone and linked to the dextran-based backbone using a thiol-maleimide conjugation. In certain aspects, at a neutral pH, the constructs retain their payloads (i.e. the therapeutic agents) long enough to carry them to a mannose-binding C-type lectin receptor (such as, for example, CD206). Once the mannose-binding C-type lectin receptor binds to the construct, the receptor/ligand complex is internalized by receptor mediated endocytosis to endosomes that become naturally acidified to a pH of about 4 to 5.5. Once inside an acidified endosome, the drug payload is released. In some aspects, the bisphosphonate carrying MADs have low toxicity to human macrophages, however, have a remarkable ability to alter their phenotype to become more proinflammatory and anti-tumor. Importantly, they also induce a highly significant reduction in expression of SIRPα (the "don't eat me" receptor for CD47) that is frequently expressed on cancer cells. Without being limited to any particular theory or mechanism, the combination of the ability to transition to a proinflammatory phenotype with the lowered expression of SIPRα suggest that TAMs exposed to the disclosed constructs will aggressively attack and phagocytize cancer cells and stimulate other immune cells, such as lymphocytes, to adopt an antitumor phenotype.

In certain implementations, the method of repolarizing a TAM comprises administering to a subject in need thereof an effective dose of a compound disclosed herein. In further embodiments, the method comprises administering a compound comprising a dextran backbone, one or more mannose-binding C-type lectin receptor targeting moieties, and a bisphosphonate compound coupled to the dextran backbone via a thiol-maleimide conjugation. In even further embodiments, the compound comprises the subunit as provided in Formula (I) disclosed herein.

In certain aspects, the compound is administered in a therapeutically effective amount. In further aspects, the compound is administered in a prophylactically effective amount.

In yet further aspects, the method further comprises administering the compound intravenously, intraperitoneally, intramuscularly, orally, subcutaneously intraocularly, intra-tumor injection or transdermally or delivered directly to tumor organ by invasive techniques.

In still further aspects, the method further comprises administering the composition in conjunction with at least one other treatment or therapy. In even further aspects, the other treatment or therapy comprises co-administering an anti-cancer agent. In further aspects, the other treatment or therapy is chemotherapy. In certain aspects, the compound is administered alone or in combination with other chemical based therapeutics or with radiation therapy or thermal therapy or physical therapy or dietary therapy.

According to further embodiments, the at least one other treatment or therapy is an immunotherapy, such as, the administration of an immunomodulatory agent. According to certain implementations, the at least one other treatment or therapy is anti-CTLA4 immunotherapy. In certain implementations, the immunomodulatory agent is an immunostimulator. In some embodiments, the immunomodulatory agent is a glucocorticoid, hydrocortisone (cortisol), cortisone acetate, prednisone, prednisolone, methylprednisolone, dexamethasone, betamethasone, triamcinolone, beclometasone, fludrocortisone acetate, deoxycorticosterone acetate (doca) aldosterone, a non-glucocorticoid steroid, a cytostatic agent, an alkylating agent, nitrogen mustard (cyclophosphamide), nitrosourea, a platinum compound, an antimetabolite, a purine analog, azathioprine, mercaptopurine, mycophenolic acid, a pyrimidine synthesis inhibitor, leflunomide, teriflunomide, a folic acid analog, methotrexate, a cytotoxic antibiotic, dactinomycin, anthracyclines, mitomycin C, bleomycin, mithramycin, an antibody or fusion thereof, anti-thymocyte globulin, anti-lymphocyte globulin, an anti-IL-2 receptor antibody, an anti-CD3 antibody, OKT3 (muromonab), otelixizumab, teplizumab, visilizumab, an anti-CD4 antibody, clenoliximab, keliximab, zanolimumab, an anti-CD11a antibody, efalizumab, an anti-CD18 antibody, erlizumab, rovelizumab, an anti-CD20 antibody, afutuzumab, ocrelizumab, ofatumumab, pascolizumab, rituximab, an anti-CD23 antibody, lumiliximab, an anti-CD40 antibody, teneliximab, toralizumab, an anti-CD40L antibody, ruplizumab, an anti-CD62L antibody, aselizumab, an anti-CD80 antibody, galiximab, an anti-CD147 antibody, gavilimomab, a B-Lymphocyte stimulator (BLyS) inhibiting antibody, belimumab, an anti-PD1 (anti-programmed cell death protein 1, or anti-CD279) antibody or antibody fragment, an anti-PD-L1 (anti-programmed death-ligand1, or anti-B7 homolog 1 (B7-H1), or anti-CD274) antibody or antibody fragment, an anti-CTLA4 (anti-cytotoxic T-lymphocyte-associated protein 4, or antiCD152) antibody or antibody fragment, an CTLA4-Ig fusion protein, abatacept, belatacept, ipilimumab, tremelimumab, an anti-eotaxin 1 antibody, bertilimumab, an anti-α4-integrin antibody, natalizumab, an anti-IL-6R antibody, tocilizumab, an anti-LFA-1 antibody, odulimomab, an anti-CD25 antibody, basiliximab, daclizumab, inolimomab, an anti-CD5 antibody, zolimomab, an anti-CD2 antibody, siplizumab, nerelimomab, faralimomab, atlizumab, atorolimumab, cedelizumab, dorlimomab aritox, dorlixizumab, fontolizumab, gantenerumab, gomiliximab, lebriliximab, maslimomab, morolimumab, pexelizumab, reslizumab, roveliximab, talizumab, telimomab aritox, vapaliximab, vepalimomab, aflibercept, alefacept, rilonacept, an immunophilin modulating agent, rapamycin, a calcincurin inhibitor, tacrolimus, ciclosporin (cyclosporin), pimccrolimus, abetimus, gusperimus, ridaforolimus, everolimus, temsirolimus, zotarolimus, a TNF inhibitor, infliximab, adalimumab, certolizumab pegol, golimumab, etanercept, thalidomide, lenalidomide, pentoxifylline, bupropion, curcumin, catechin, an IL-1 receptor antagonist, anakinra, an anti-IL-5 antibody, mepolizumab, an IgE inhibitor, omalizumab, talizumab, an IL12 inhibitor, an IL23 inhibitor, ustekinumab, an opiod, an IMPDH inhibitor, mycophenolic acid, myriocin, fingolimod, an NF-κB inhibitor, raloxifene, drotrecogin alfa, denosumab, an NF-κB signaling cascade inhibitor, disulfiram, olmesartan, dithiocarbamate, a proteasome inhibitor, bortezomib, MG132, Pro1, NPI-0052, curcumin, genistein, resveratrol, parthenolide, thalidomide, lenalidomide, flavopiridol, nonsteroidal anti-inflammatory drugs (NSAIDs), arsenic trioxide, dehydroxymethylepoxyquinomycin (DHMEQ), 13C (indole-3-carbinol)/DIM (di-indolmethane) (13C/DIM), Bay 11-7082, luteolin, cell permeable peptide SN-50, IκBα-super repressor overexpression, NFκB decoy oligodeoxynucleotide (ODN), or a derivative or analog of any thereof.

In exemplary implementations, the combined administration of the compound and the at least one treatment or therapy is synergistically or additively more effective relative to administration of either alone.

According to certain embodiments, administration of the compounds disclosed herein in conjunction with another therapy or treatment is associated with reduced toxicity compared to administration of the other therapy or treatment alone. In further embodiments, the co-administration of the instantly disclosed compounds and other therapy or treatment produce a synergic effect. In yet further embodiments, the co-administration of the instantly disclosed compounds and provides for lower effective dose of the other therapy or treatment.

The methods provided herein may be practiced in an adjuvant setting. In some embodiments, the method is practiced in a neoadjuvant setting, i.e., the method may be carried out before the primary/definitive therapy. In some embodiments, the method is used to treat an individual who has previously been treated. Any of the methods of treatment provided herein may be used to treat an individual who has not previously been treated. In some embodiments, the method is used as a first line therapy. In some embodiments, the method is used as a second or later line therapy.

In further embodiments, a method of treating a disease is provided. In some embodiments, the method comprises administering to a subject in need thereof an effective amount of a compound as disclosed herein. In some aspects, the disease is cancer, an autoimmune disease, or an inflammatory disorder.

According to other aspects, the subject has been diagnosed with melanoma, breast cancer, lung carcinoma, pancreatic carcinoma, renal carcinoma, ovarian, prostate or cervical carcinoma, glioblastoma, or colorectal carcinoma, cerebrospinal tumor, head and neck cancer, thymoma, mesothelioma, esophageal cancer, stomach cancer, liver cancer, pancreatic cancer, bile duct cancer, bladder cancer, testicular cancer, germ cell tumor, ovarian cancer, uterine cervical cancer, endometrial cancer, lymphoma, acute leukemia, chronic leukemia, multiple myeloma, sarcoma, or any combination thereof.

In certain aspects, the method further comprises administering the composition as a bolus and/or at regular intervals. In certain aspects, the disclosed method further comprises administering the composition intravenously, intraperitoneally, intramuscularly, orally, subcutaneously, intra-tumorally or transdermally.

According to certain further embodiments, the method further comprises diagnosing the subject with cancer. In further aspects, the subject is diagnosed with cancer prior to administration of the composition. According to still further aspects, the method further comprises evaluating the efficacy of the composition. In yet further aspects, evaluating the efficacy of the composition comprises measuring tumor size prior to administering the composition and measuring tumor size after administering the compound. In even further aspects, evaluating the efficacy of the composition occurs at regular intervals. According to certain aspects, the disclosed method further comprises optionally adjusting at least one aspect of method. In yet further aspects, adjusting at least one aspect of method comprises changing the dose of the composition, the frequency of administration of the composition, or the route of administration of the compound.

According to certain alternative embodiments, the subject has been diagnosed with a disease associated with elevated levels of CD206+ macrophages, dendritic cells and/or myeloid derived suppressor cells (MDSC) or with a disease for which such CD206+ cell types contribute to the pathobiology of the illness. Such diseases or conditions include, but are not limited to: acquired immune deficiency syndrome (AIDS), acute disseminated encephalomyelitis (ADEM), Addison's disease, agammaglobulinemia, allergic diseases, alopecia areata, Alzheimer's disease, amyotrophic lateral sclerosis, ankylosing spondylitis, antiphospholipid syndrome, antisynthetase syndrome, arterial plaque disorder, asthma, atherosclerosis, cardiovascular disease, atopic allergy, atopic dermatitis, autoimmune aplastic anemia, autoimmune cardiomyopathy, autoimmune enteropathy, autoimmune hemolytic anemia, autoimmune hepatitis, autoimmune hypothyroidism, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenia purpura, autoimmune urticarial, autoimmune uveitis, Balo disease/Balo concentric sclerosis, Behcet's disease, Berger's disease, Bickerstaffs encephalitis, Blau syndrome, bullous pemphigoid, Castleman's disease, celiac disease, Chagas disease, chronic inflammatory demyelinating polyneuropathy, chronic recurrent multifocal osteomyelitis, chronic obstructive pulmonary disease, chronic venous stasis ulcers, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's Syndrome, cutaneous leukocytoclastic angiitis, Dego's disease, Dercum's disease, dermatitis herpetiformis, dermatomyositis, Diabetes mellitus type I, Diabetes mellitus type II diffuse cutaneous systemic sclerosis, Dressler's syndrome, drug-induced lupus, discoid lupus erythematosus, eczema, emphysema, endometriosis, enthesitis-related arthritis, eosinophilic fasciitis, eosinophilic gastroenteritis, eosinophilic pneumonia, epidermolysis bullosa acquisita, erythema nodosum, erythroblastosis fetalis, essential mixed cryoglobulinemia, Evan's syndrome, fibrodysplasia ossificans progressive, fibrosing alveolitis (or idiopathic pulmonary fibrosis), gastritis, gastrointestinal pemphigoid, Gaucher's disease, glomerulonephritis, Goodpasture's syndrome, Graves' disease, Guillain-Barré syndrome (GBS), Hashimoto's encephalopathy, Hashimoto's thyroiditis, heart disease, Henoch-Schonlein purpura, herpes gestationis (aka gestational pemphigoid), hidradenitis suppurativa, HIV infection, Hughes-Stovin syndrome, hypogammaglobulinemia, infectious diseases (including bacterial, viral, parasitic, and helminthic infectious diseases), idiopathic inflammatory demyelinating diseases, idiopathic pulmonary fibrosis, idiopathic thrombocytopenia purpura, IgA nephropathy, inclusion body myositis, inflammatory arthritis, inflammatory bowel disease, inflammatory dementia, interstitial cystitis, interstitial pneumonitis, juvenile idiopathic arthritis (aka juvenile rheumatoid arthritis), Kawasaki's disease, Lambert-Eaton myasthenic syndrome, leukocytoclastic vasculitis, lichen planus, lichen sclerosus, linear IgA disease (LAD), lupoid hepatitis (aka autoimmune hepatitis), lupus erythematosus, lymphomatoid granulomatosis, Majeed syndrome, malignancies including cancers (e.g., sarcoma, Kaposi's sarcoma, lymphoma, leukemia, carcinoma and melanoma), Meniere's disease, microscopic polyangiitis, Miller-Fisher syndrome, mixed connective tissue disease, morphea, Mucha-Habermann disease (aka Pityriasis lichenoides et varioliformis acuta), multiple sclerosis, myasthenia gravis, myositis, narcolepsy, neuromyelitis optica (aka Devic's disease), neuromyotonia, ocular cicatricial pemphigoid, opsoclonus myoclonus syndrome, Ord's thyroiditis, palindromic rheumatism, PANDAS (pediatric autoimmune neuropsychiatric disorders associated with streptococcus), paraneoplastic cerebellar degeneration, Parkinsonian disorders, paroxysmal nocturnal hemoglobinuria (PNH), Parry Romberg syndrome, Parsonage-Turner syndrome, pars planitis, pemphigus vulgaris, peripheral artery disease, pernicious anaemia, perivenous encephalomyelitis, POEMS syndrome, polyarteritis nodosa, polymyalgia rheumatic, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restenosis, restless leg syndrome, retroperitoneal fibrosis, rheumatoid arthritis, rheumatic fever, sarcoidosis, schizophrenia, Schmidt syndrome, Schnitzler syndrome, scleritis, scleroderma, sepsis, acute respiratory distress syndrome (ARDS), serum Sickness, Sjögren's syndrome, spondyloarthropathy, Still's disease (adult onset), stiff person syndrome, stroke, subacute bacterial endocarditis (SBE), Susac's syndrome, Sweet's syndrome, Sydenham chorea, sympathetic ophthalmia, systemic lupus erythematosus, Takayasu's arteritis, temporal arteritis (aka "giant cell arteritis"), thrombocytopenia, Tolosa-Hunt syndrome,) transplant (e.g., heart/lung transplants) rejection reactions, transverse myelitis, tuberculosis, ulcerative colitis, undifferentiated connective tissue disease, undifferentiated spondyloarthropathy, urticarial vasculitis, vasculitis, vitiligo, and Wegener's granulomatosis.

Further provided are methods of making the compounds as disclosed herein. In certain embodiments, the methods of making the compound according to Formula (I) may comprise the following steps: (a) synthesizing a dextran backbone having one or more amine terminated leashes attached thereto; (b) synthesizing a bisphosphonate compound comprising a carbonyl functional group; (c) reacting the carbonyl functional group with an acylhydrazide to form a bisphosphonate compound modified with a hydrazone moiety; (d) modifying one or more amine terminated leashes with a maleimide moiety; and (e) substituting one or more maleimide moieties from step (d) with the bisphosphonate compound modified with the hydrazone moiety from step (c) through a thiol-maleimide conjugation.

In an aspect, the steps (a) through (e) do not need to occur in the exact same order. In further aspects, additional steps may occur between each of steps (a) through (e). In some embodiments, step (d) may occur before step (b), after step (b), before step (c), or after step (c). In further embodiments, step (a) occurs prior to any of steps (b) through (e). In further embodiments, step (c) occurs after any of steps (a) through (d).

In certain implementations, the bisphosphonate compounds are prepared with a hydrazone prior to being attached to the MAD constructs. In further aspects, the bisphosphonate compound is substituted with a carbonyl functional group prior to being modified to the hydrazone moiety. In some implementations, the MAD constructs are prepared with at least one leash attached to a maleimide moiety prior to adding the bisphosphonate compound. In exemplary embodiments, the bisphosphonate compounds modified with a hydrazone moiety is attached to the MAD construct via a thiol-maleimide conjugation.

In some embodiments, mannose-binding C-type lectin receptor targeting moieties are further attached to one or more amine terminated leashes. In certain embodiments, the mannose-binding C-type lectin targeting moieties are attached to between about 15% and about 70%, between about 17% and about 65%, or about 20% and about 60% of the glucose residues via the amine terminated leashes. In further embodiments, the mannose-binding C-type lectin targeting moieties are attached to up to about 60%, up to about 70%, up to about 80%, up to about 90%, or up to about 100% of the glucose residues via the amine terminated leashes. In certain aspects, the percentages may vary depending on the size of the dextran backbone.

Additional discussion regarding the methods of making the compounds may be found within the non-limiting Examples provided herein.

All publications and patent applications in this specification are indicative of the level of ordinary skill in the art to which this disclosure pertains. All publications and patent applications are herein incorporated by reference to the same extent as if each individual publication or patent application was specifically and individually indicated as incorporated by reference.

EXAMPLES

Embodiments of the present disclosure are further defined in the following non-limiting Examples. It should be understood that these Examples, while indicating certain embodiments of the disclosure, are given by way of illustration only. From the above discussion and these Examples, one skilled in the art can ascertain the essential characteristics of this disclosure, and without departing from the spirit and scope thereof, can make various changes and modifications of the embodiments of the disclosure to adapt it to various usages and conditions. Thus, various modifications of the embodiments of the disclosure, in addition to those shown and described herein, will be apparent to those skilled in the art from the foregoing description. Such modifications are also intended to fall within the scope of the appended claims.

Mannosylated amine dextrans (MADs) carrying bisphosphonate payloads (MAD-BIS) as drug delivery constructs targeted to CD206 expressing cells were synthesized under three parts: (1) Synthesis of the MAD backbones; (2) Synthesis of the bisphosphonate drug payloads; and (3) Modification of the MAD backbone and the bisphosphonate drug payloads to enable their linking with a pH sensitive hydrazone linker using a thiol-maleimide conjugation. After the MAD-BIS synthesis was completed, the MAN-BIS constructs were assessed to determine their ability to release their bisphosphonate payloads at physiologic temperatures (about 37° C.) and in the mildly acidic conditions found in endosomes.

Example 1: Synthesis of the MAD-BIS-1 and MAD-BIS-2 Drug Delivery Constructs

Synthesis of the MAD backbones: Beginning with a 10 kDa (Mw) dextran, MAD backbones were synthesized as described in U.S. Pat. No. 6,409,990 (which was previously incorporated by reference in its entirety) for mannosylated amine DTPA dextran, with the exception that the conjugation of a chelating agent (i.e. DTPA) was omitted. The resulting construct had a combination of (1) glucose moieties modified by the attachment of amine terminated leashes to which mannose moieties were conjugated, (2) glucose moieties with amine terminated leashes to which mannose moieties were not conjugated (i.e. free amine terminated leashes), and (3) unmodified glucose moieties without either amine terminated leashes or conjugated mannose. The resulting construct had the following structure:

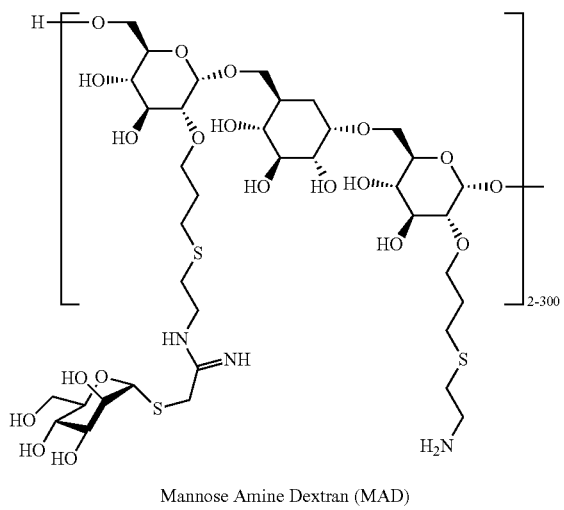

Mannose Amine Dextran (MAD)

The free amine terminated leashes could be later utilized as points of attachment for drug payloads via degradable linkers. For simplicity in the above structure, the amine terminated leashes are shown attached to the C2 hydroxyl groups of the glucose moieties in the dextran polymer; however, these leashes may be distributed to any of the hydroxyl groups of the MAD backbone. In this example, the MAD backbone had approximately 36 amine terminated leashes to which an average of 22 mannose moieties were attached, leaving about 14 free amines. The multiple mannose moieties were required to enable high affinity binding to CD206. The MAD backbone also had an average of about 16 glucose moieties that were not modified by the addition of an amine terminated leash. This MAD backbone construct is provided only as an example. MAD backbones suitable for drug delivery of bisphosphonate payloads to CD206 expressing cells can be constructed using initial dextran polymers that range from 1 kDa to greater than 150 kDa in average molecular weight (Mw). Changing the initial Mw of the starting dextran dictates the final size (Mw) of the final drug delivery construct. Drug delivery vehicles of differing Mw vary in their biodistribution when administered to either animal or human subjects. These differences in biodistribution may permit optimizing the drug delivery vehicle for varying pharmacological applications. In addition, the number of amine terminated leashes and/or the number of conjugated mannose moieties can be purposefully changed in theory to range from zero to the number of hydroxyl groups on the glucose moieties of the initial dextran. Changing the numbers of free amines and mannose moieties will also change biodistributions and CD206 receptor affinities, which may permit optimizing the drug delivery vehicle for varying pharmacological applications.

Syntheses of bisphosphonate drug payloads (BIS-1 and BIS-2): To form a hydrazone linkage with desirable hydrolysis kinetics, one coupling partner-either the drug or the dextran backbone-bears a carbonyl moiety, while the other bears a hydrazide moiety. Since commercially available bisphosphonates, including zoledronate, do not contain either of these groups, the bisphosphonates BIS-1 and BIS-2 were prepared with ketone functionality on an aromatic ring as payloads for the MAD-BIS CD206 targeted drug delivery vehicles. All reagents used to synthesize these new bisphosphonates were purchased from commercial vendors. The syntheses of both were initiated by adding an arylamine to tetraethyl vinylidene bisphosphate as shown in FIG. 1. For the first bisphosphonate (BIS-1), 2-amino-4-methyl-5-acetyl thiazole was combined with tetraethyl vinylidene bisphosphonate in N,N-dimethylformamide (DMF) and heated at 70° C. with constant stirring for 15 hours. The contents were cooled, and the consumption of the starting vinylidene was confirmed by thin-layer chromatography (5% MeOH/DCM, KMnO4 staining). The reaction slurry was then dry loaded onto 20 g of silica. Column purification with a 2-10% methanol-dichloromethane gradient provided the protected desired addition product as a clear oil (3.24 g, 85%).

To remove ethyl phosphonate protection, 0.973 g (2.13 mmol) of the purified oil was dissolved in 16 ml of anhydrous acetonitrile (ACN) under nitrogen and 8 equivalents (2.25 ml, 17 mmol) of trimethylsilyl bromide (TMSBr) were added dropwise. Completion of the reaction was confirmed by LC-MS at 4 hours and the solution concentrated in vacuo. Precipitation with water and acetone provided compound BIS-1,2-(4-methyl-5-acetylthiazole-2-yl-amino)ethylidene 1,1-bisphosphonic acid as an off-white powder (606 mg, 83%).

The synthesis of BIS-2,2-(4-acetylimidazole)ethylidene-1-methyl-1,1-bisphosphonic acid, is further shown in FIG. 1. BIS-2 was made by combining 1 g (3.3 mmol) of vinylidene bisphosphonate and 0.55 g (5.0 mmol) of 4-acetylimidazole in a pressure bottle with 20 ml of anhydrous tetrahydrofuran (THF). The bottle was sealed and heated at 75° C. while stirring for 3 hours. The contents were cooled, and acceptable reaction progress was confirmed by ESI+ LC-MS. The reaction was filtered to remove excess imidazole and concentrated in vacuo. The crude material (1.13 g, ~70% HPLC purity) was not stable to purification efforts, instead eliminating to the starting 4-acetylimidazole and vinylidene. The addition of non-hydrogen functionality at the alpha position was thus required. Therefore, prior to purification, the crude intermediate was reconstituted in 35 ml of anhydrous DMF, cooled to −40° C. and 88 mg of 60% sodium hydride (NaH) dispersion in oil (53 mg, 2.2 mmol) was added. After stirring about 10 minutes, 0.14 ml (2.2 mmol) of methyl iodide (MeI) was added, stirred for 15 minutes and allowed to equilibrate to ambient temperature over 1 hour. The crude product was stable to purification via silica column chromatography with 5% methanol in dichloromethane yielding 154 mg (11% overall yield) of pure methylated protected bisphosphonate as a pale-yellow oil.

The isolated yield of the aforementioned BIS-2 synthesis was impacted by the formation of by-products during the methylation reaction. The following serves as an alternative synthesis whereby the imidazole ketone is protected as a ketal (1,3-dioxolane, 3) prior to addition to the vinylidene.

To prepare N-pivaloyloxymethyl (POM) protected 4-acetylimidazole (1), 5.0 g (45.4 mmol) of 4-acetylimidazole was suspended in 100 ml of anhydrous THF and cooled on an ice bath. 1.2 equivalents of NaH (1.31 g, 54.5 mmol, 2.18 g of 60% dispersion in oil) was added and the suspension stirred under nitrogen atmosphere for 40 minutes. 1.2 equivalents (54.5 mmol, 7.85 ml) of chloromethyl pivalate was added, stirred for 30 minutes on the ice bath and the reaction continued overnight at ambient temperature. The contents of the flask were diluted with ethyl acetate and saturated sodium bicarbonate, and the organics washed with brine, dried over anhydrous sodium sulfate and concentrated to an off-white solid. 9.04 g (89%) of POM-protected acetylimidazole (1) were obtained as white needles in a single crystallization from boiling ethyl acetate and hexanes.

4.88 g (21.8 mmol) of POM-protected acetylimidazole (1) was combined under nitrogen with 70 ml of freshly distilled ethylene glycol and 25 ml of anhydrous dichloromethane (DCM). 8 equivalents (0.174 mol, 22 ml) of trimethylsilyl chloride were added over a few minutes and the opaque solution was left to stir under nitrogen and at ambient temperature overnight. The reaction was concentrated in vacuo and placed on hi-vacuum to remove excess reagent followed by dilution with saturated sodium bicarbonate and product extraction with DCM. The organics were washed and dried with saturated brine and anhydrous sodium sulfate, filtered, and concentrated providing 3.42 g of an off-white solid. Crystallization from warm ethyl acetate and hexanes provided 2.44 g (42%) of the fully protected ketal product (2) as a white powder.

POM removal was achieved by dissolving 2.28 g (8.5 mmol) of the fully protected imidazole (2) in 45 ml of 7 M ammonia in methanol, sealing the flask, and stirring overnight at room temperature. The reaction was complete by sensitive ESI+ LC-MS and concentrated two times in vacuo with methanol without a water bath. The solid residue was dissolved in a small volume of methanol on a 50° C. water bath and allowed to equilibrate to ambient temperature while stirring unsealed and open to the air. The flask was sealed and placed in a −20° C. freezer to crystallize further. 756 mg (58% yield) of 5-(2-methyl-1,3-dioxolan-2-yl)-1H imidazole (3) as a bright white powder was recovered after filtration and placed on hi-vacuum (Calc. mass 154.07, found ESI+ LC-MS [M+1] 155.09).

To 55 mg (0.36 mmol) of 5-(2-methyl-1,3-dioxolan-2-yl)-1H imidazole (3) in 1 ml of anhydrous THF under nitrogen atmosphere was added 106 mg (0.35 mmol) of tetraethyl vinylidene-1,1-bisphosphonate in 1 ml of anhydrous THF. After stirring at room temperature for 2 hours, satisfactory addition product had formed by sensitive ESI+ LC-MS. The flask was cooled on an ice-bath and 1.05 equivalents (9 mg, 0.37 mmol, 15 mg of 60% dispersion in oil) of NaH was charged and stirred for 15 minutes. 1.5 equivalents (0.53 mmol, 33 μL) of iodomethane were then added to the reaction mixture and removed from the ice-bath to stir overnight. The mixture was diluted with DCM and 0.1 M pH 7 PBS, the organics washed with brine, dried over anhydrous sodium sulfate and concentrated in vacuo. A gradient of 0 to 10% MeOH in DCM on a 10 g silica column resulted 99 mg (59% yield) of the fully-protected BIS-2 product as clear oil (Calc. 468.18, found ESI+ LC-MS [M+1] 469.28).

To deprotect the phosphonate groups, 0.148 g (0.349 mmol) of the purified oil was dissolved in 2.7 ml of anhydrous acetonitrile (ACN) under nitrogen and 8 equivalents (0.37 ml, 2.8 mmol) of trimethylsilyl bromide (TMSBr) were added dropwise. Reaction completion was confirmed by LC-MS at 4 hours and the solution concentrated in vacuo. With ketal protection, the reaction was diluted with water and lyophilized after completion of phosphonate deprotection. The crude material was purified by C-18 reverse phase chromatography using water as a mobile phase. Pure fractions were combined, frozen, and lyophilized, providing BIS-2 as a light green powder (74.4 mg).

Figure 2:
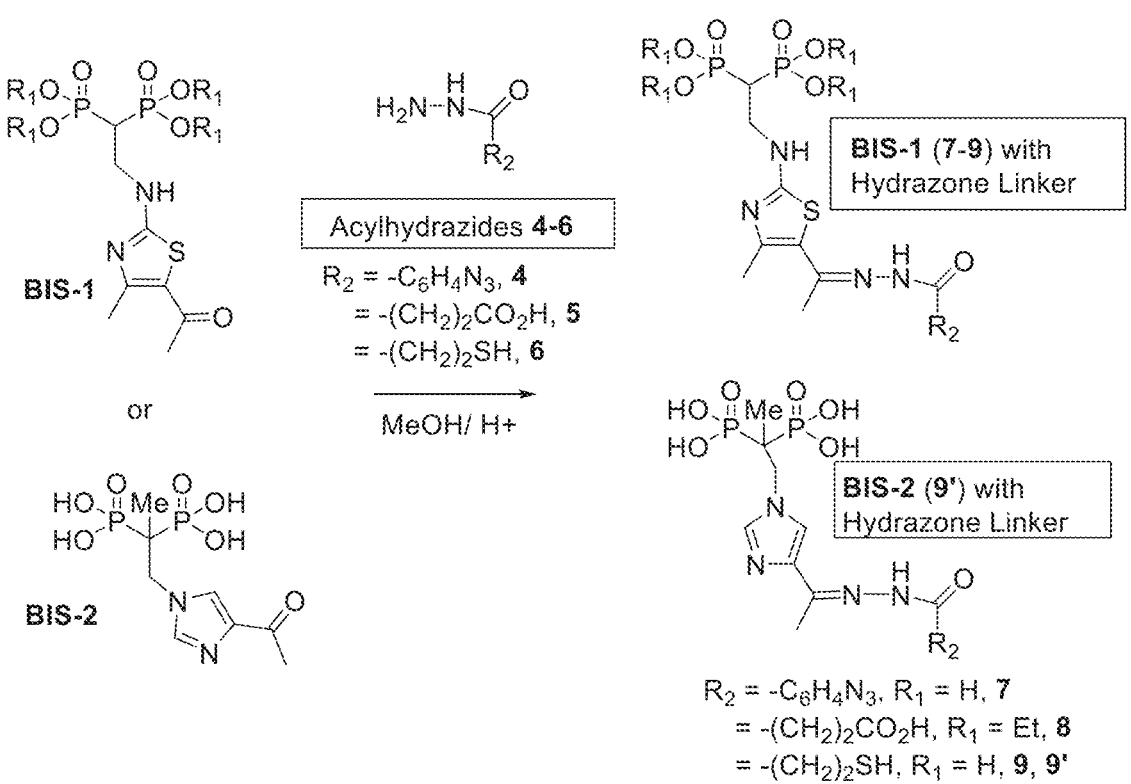
FIG. 2 shows the preparation of hydrazone linkages to BIS-1 and BIS-2. Three linkers were evaluated with differing modes of conjugation to MAD backbones. The linker terminated with a free thiol group in combination with a maleimide modified MAD backbone was able to successfully conjugate bisphosphonates.

Modification of MAD backbones and bisphosphonate drug payloads to enable their linking via a pH sensitive hydrazone linkers: BIS-1 and BIS-2 were further modified to incorporate a pH sensitive hydrazone and functionality for linkage to MADs as shown in FIG. 2. The hydrazones of BIS-1 and BIS-2 (7-9 and 9') were successfully prepared via condensation with acylhydrazides (4-6) that differ in the sidechain ($R_2$) functionality and therefore the chemical strategies for attachment to a MAD backbone. However, subsequent attempts to link BIS-1 hydrazone azide (7) via a click chemistry method disclosed in U.S. Patent Application Ser. No. 63/294,996 were not successful. Direct coupling of BIS-1 hydrazone (8) carboxylic acid as well as hydrazone formation through condensation reactions of the carbonyl groups on BIS-1 and BIS-2 with hydrazide bound to the MAD backbone also failed to deliver the desired conjugation products.

Figure 3:
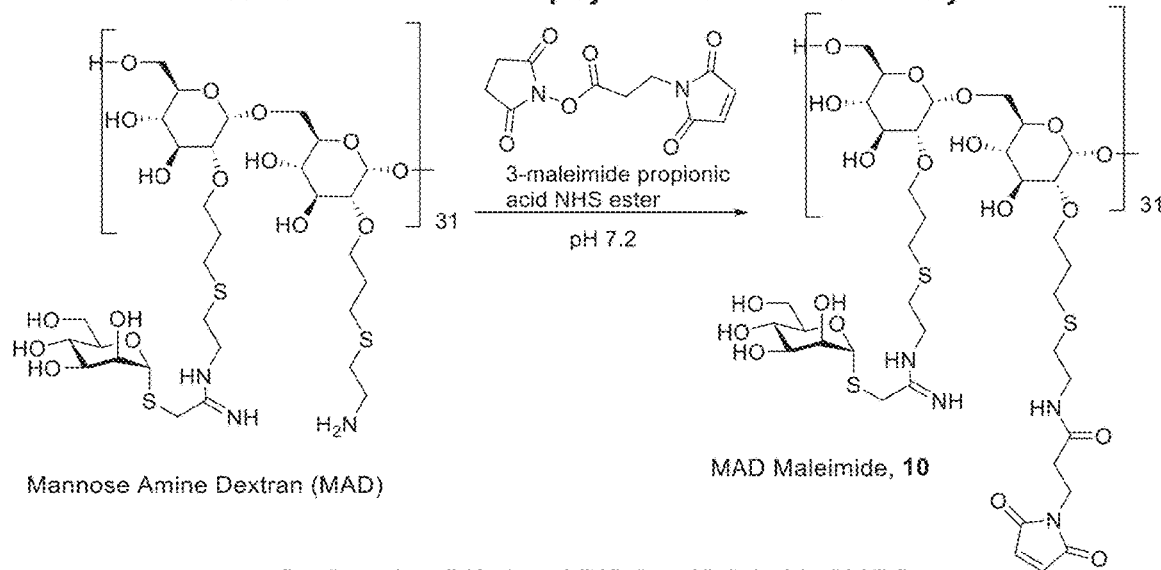
FIG. 3 shows the conjugation of BIS-1 and BIS-2 with hydrazone linkers and terminal thiol groups to the MAD modified to display terminal maleimide moieties.
Figure 3:
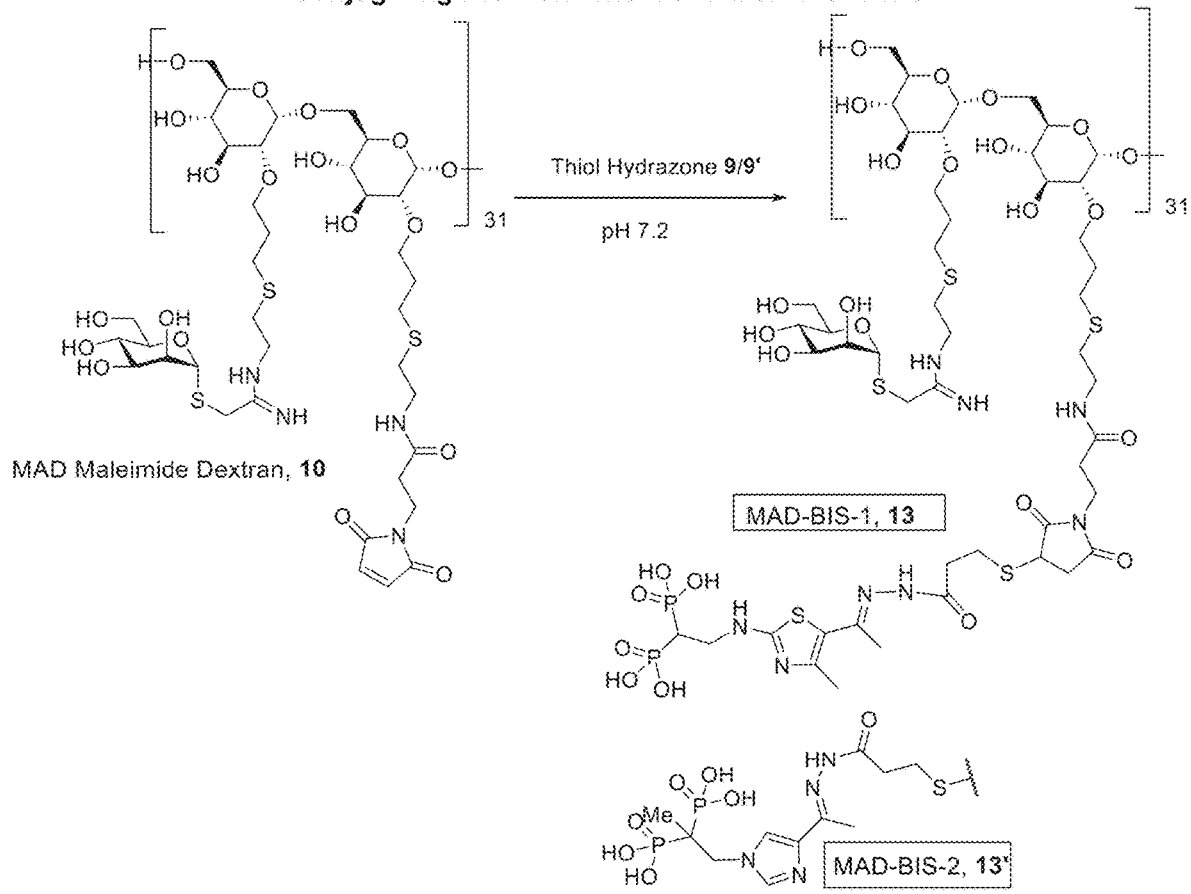

However, the conjugation of BIS-1 and BIS-2 hydrazones (9) and (9') to MADs were successful using a thiol-maleimide conjugation as shown in FIG. 3. The thiol coupling partner was deliberately positioned on hydrazone (9/9') and maleimide on MAD since the reverse would permit unreacted thiol bound to the backbone to crosslink as disulfides after conjugation. MAD backbones were first modified by addition of maleimide moieties to the free amine terminated leashes as shown in FIG. 3. In a second step, (9) or (9') was charged to an aqueous solution containing the maleimide derivatized MAD.

To prepare MAD-BIS-1 (13), 90 mg of mannose dextran (MAD) (1H NMR: Ave. 22-mannose, 14 amines, Mw 19,393 g/mol) was dissolved in 3.6 ml of 0.05 M PBS buffer (pH 7.2) and the pH adjusted with minimal volumes of phosphoric acid and 1 N NaOH to 7.0. In a separate flask under inert atmosphere, 33 mg (0.195 mmol) of 3-maleimidopropionic and 24 mg (0.205 mmol) of N-hydroxysuccinimide were solubilized in 0.28 ml of anhydrous DMF. 39 mg (0.205 mmol) of N-(3-Dimethylaminopropyl)-N'-ethylcarbodiimide hydrochloride (EDC·HCl) was added, the flask sealed, and the activation stirred for 1 hour at room temperature. The entire DMF solution of 3-maleimidopropionic acid N-hydroxysuccinimide ester (3 equivalents of NHS ester versus the amine concentration on dextran) was charged to the flask containing the mannose dextran. Reaction progress was monitored by following the complete loss of amine content in the solution. At completion, the reaction was transferred to a 10 kDa MWCO Amicon centrifugal spin-filter, diluted to 12 ml with 0.05 M PBS buffer (pH 7.1) and concentrated to approximately 0.5 ml volume. The ultrafiltration was repeated two more cycles and the final retentate containing MAD maleimide (10) was transferred from the spin-filter and diluted to 3 ml with 0.05 M PBS buffer (pH 7.1). 58 mg (0.130 mmol), two equivalents versus maleimide content on (10) of bisphosphonate hydrazone (9) was added and allowed to stir at ambient temperature for 1.5 hours. The reaction was diluted to 12 ml with distilled water and concentrated to 0.5 ml in a 10 kDa MWCO centrifugal spin-filter. The retentate was washed an additional 5 times with distilled water, passed through a 0.45 μm syringe filter, frozen and lyophilized providing 76.8 mg of MAD-BIS-1 (13). The construct had an average of 6.3 BIS-1 moieties per MAD as determined by HPLC analysis after complete hydrolysis from the backbone. The synthesis of MAD-BIS-2 (13') followed the same procedure substituting BIS-2 hydrazone (9'). 53.5 mg of MAD-BIS-2 (13') was prepared averaging 6.0 BIS-2 moieties per dextran.

An important distinction between this chemical method and those disclosed in U.S. Pat. No. 10,806,803 or current scientific literature, is that in previous literature, the hydrazine moiety is first attached to the drug delivery vehicle (the MAD backbones in this case) to create a point of attachment as a hydrazone with the drug payload in a second step. In certain embodiments of the present disclosure, the hydrazone linker is created as a derivative of the drug payload and, subsequently, the drug-hydrazone construct is attached to the drug delivery vehicle using a different chemistry than is described in prior literature. Furthermore, the entire linker that attaches the drug payload to the amine terminated leashes on the MAD backbone in the final synthesis product is unique. All three hydrazone linkers shown in FIG. 2 contained the same hydrazone moiety, however, had different side changes ($R_2$) to facilitate attachment to the maleimide modified MAD backbone shown in FIG. 3. However, the results demonstrated that not all $R_2$ group strategies enabled linking to the dextran backbone. Successful conjugation was only achieved between thiol-terminated $R_2$ group (6) and MAD maleimide (10). This observation highlights the unexpected results achieved with the constructs of the present disclosure as only the thiol hydrazone (6) succeeded. Therefore, the success of the thiol hydrazone (6) in light of the failures of the other two $R_2$ groups was surprising.

Release of Bisphosphonates from MAN-BIS-1 at pH 4.65 (37° C.): After synthesis of MAN-BIS-1 was complete, a sample was evaluated by HPLC. Examination of the HPLC results determined that MAN-BIS-1 was free of BIS-1 and BIS-1 with the hydrazone linker. A 1 mg/ml solution of MAN-BIS-1 in IN HCl was then then evaluated after 1 hour and 2 hours to determine the amount of BIS-1 that was released. All of the BIS-1 should have been released under these highly acidic conditions. It was determined that the amount of released BIS-1 under these highly acidic conditions was 9.2% wt/wt or >6 BIS-1 moieties per MAD backbone.

Figure 4:
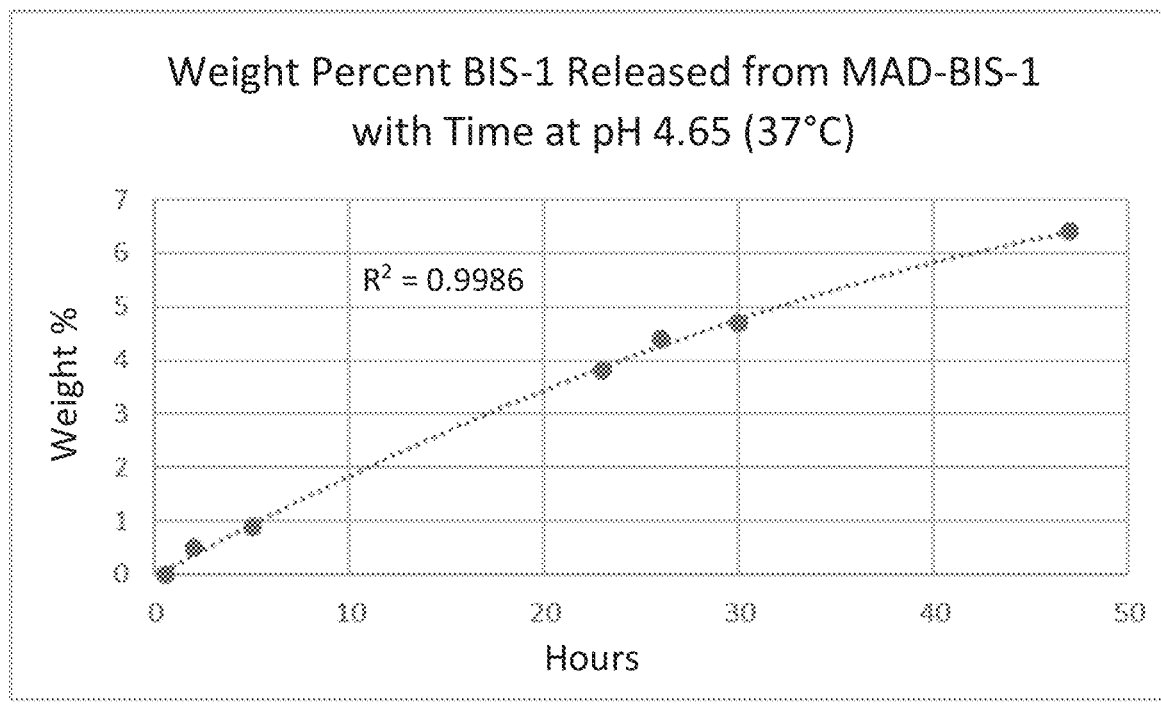
FIG. 4 shows a graph of the release of BIS-1 from MAD-BIS-1 over time at a pH 4.65.

An experiment was then performed in which MAD-BIS-1 was dissolved in an aqueous solution at pH 4.65. Samples were analyzed after various times of exposure to pH 4.65. The amount of released BIS-1 over time was monitored by HPLC. Free BIS-1 was not detected at 5 and 30 minutes but was observed after 2 hours of incubation at pH 4.65. The release was monitored over 47 hours as shown in FIG. 4. BIS-1 was gradually released over the duration of the experiment. After 47 hours of incubation, 6.4% by weight (>4 drug moieties per dextran chain) of free BIS-1 was detected by HPLC.

This observation highlights an important feature of the constructs, as they permit gradual and continuous release of the drug payload into CD206 expressing cells, which would not have been possible if the drug were not delivered on a MAD backbone. If BIS-1 or any other bisphosphonate were administered without the MAD delivery construct, it would clear quickly from the blood and localize to the bones. With the MAD-BIS constructs, there is continuous drug exposure to CD206 expressing cells for a relatively long duration.

Example 2: Bisphosphonate 1 (MAD-BIS-1)-Evaluations in Human Macrophage Cell Culture Assays MAD-BIS-1 was evaluated in a human macrophage cell culture assay. In this assay, human peripheral blood monocytes (hPBMCs) were incubated for five days in RPMI+10% FBS+1×Penicillin/Streptomycin/L-glutamine+50 ng/ml GM-CSF (complete medium) at a concentration of 500,000 monocytes per well in 48 well tissue culture plates. During this five-day incubation, the monocytes differentiated into macrophages. GM-CSF induces the macrophages to adopt an activated phenotype that is intermediate between the extremes of M1 or M2. After the five-day incubation, the medium was removed and replaced with complete medium supplemented with various concentrations of MAD-BIS-1 or unbound BIS-1 (Free-Bis-1). Saline and Vehicle (MAD without a drug payload, 80 μg/ml) were added as alternative supplements to other cultures as negative controls. The macrophage cell cultures were incubated with the supplemented complete medium for 24 hours after which it was removed and replaced with fresh complete medium. The macrophage cultures were then incubated for an additional three days. The three-day post treatment incubation was performed to permit assessment of durable changes in macrophage phenotypes. After the additional three-day incubation in fresh complete medium, the cells were harvested and evaluated by flow cytometry for viability (DAPI-) or expression of macrophage surface markers that are representative of markers that frequently considered indicative of either M1-like or M2-like phenotypes or are known immune checkpoint receptors.

The evaluated cell surface markers were CD206, CD163, CD80, CD86, MHC1, MHC2, SIRPα, and PD-1 using antibodies specific for each marker. Although the amount observed of each surface marker varied considerably between markers and between treatment groups, nearly all live cells expressed detectable amounts of all markers. The marker with the lowest expression in saline and vehicle treated controls was PD-1. The outputs of the flow cytometry assays were mean fluoresce intensities (MFI). Macrophages differentiated from monocytes collected from 3 separate donors were evaluated for all treatments. For each donor's macrophages, all experiments were run in triplicate.

Results: In all replicates of this experiment, the large majority of macrophages treated with the saline control survived to the end of the experiment (9 days). For cell viability and for all surface markers evaluated, the results for the drug free vehicle treated control were not statistically different from those observed for the saline (no drug) control, indicating that the drug free vehicle did not have pharmacological activity observed in this study. Furthermore, neither MAD-BIS-1 nor free BIS-1 decreased cell viability at any tested concentration.

Figure 5:
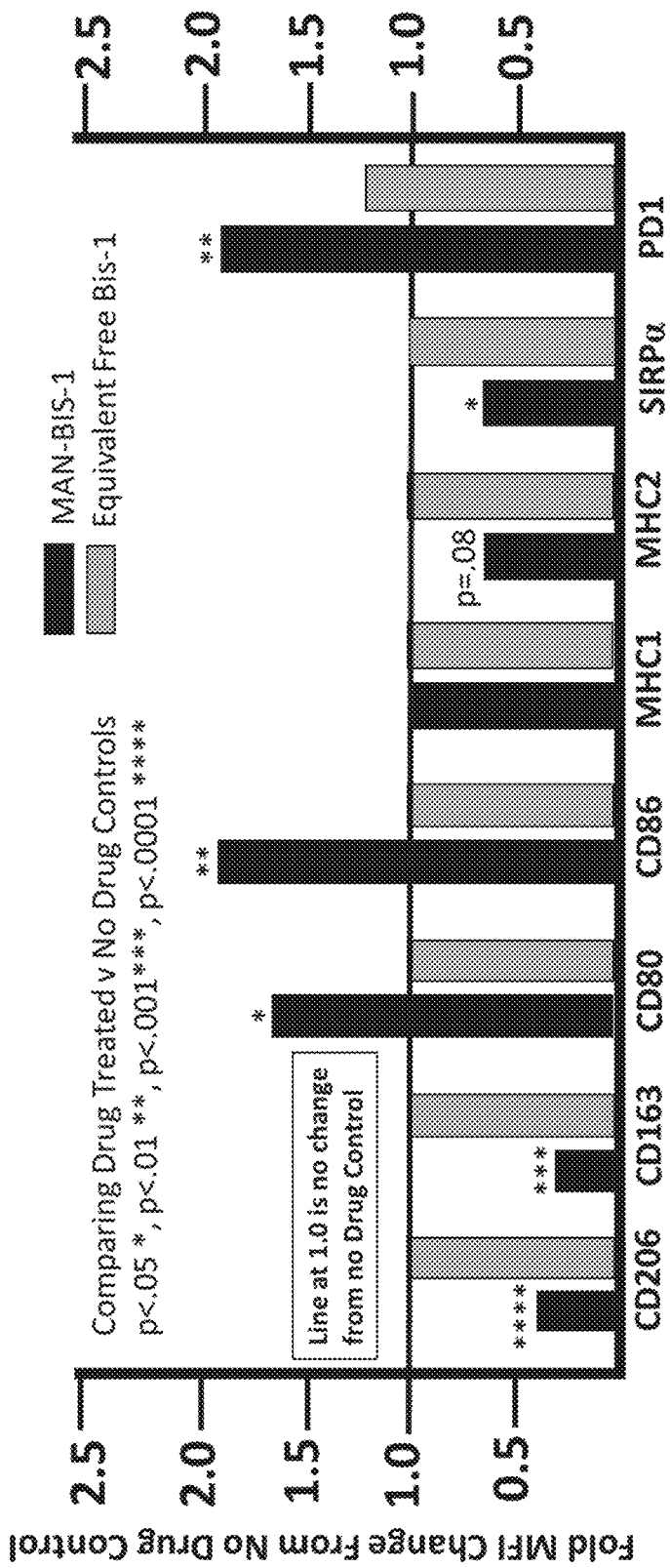
FIG. 5 shows a graph of how the various treatments with either MAN-BIS-1 or free BIS-1 affected the level of expression of eight evaluated surface markers, CD206, CD163, CD80, CD86, MHC1, MHC2, SIRPα, and PD1. All experiments were run in triplicate with macrophages from 3 human donors.

FIG. 5 shows an aggregate representation of how the various treatments with either MAD-BIS-1 or free BIS-1 affected the level of expression of the eight evaluated surface markers. The values shown are the average fold change in expression (MFI) compared to the MFI values observed in the saline controls. The statistical significance of these changes in expressions was measured by Z tests.

The data shown in FIG. 5 demonstrate the fold changes in expression of the indicated surface markers treated with either 80 µg of MAD-BIS-1 or an equal molar amount of free BIS-1 not attached to the mannosylated amine dextran vehicle. A fold change of 1.0 indicated that there was no change in expression; the average level of expression (MFI) observed in the treated cells was the same as what was observed in the saline controls. A value of 2.0 means that the average MFI of the treated cells was twice that of the MFI observed in the saline treated controls. Conversely, a value of 0.5 means that the MFI observed in the treated cells was half that observed in the saline controls.

Several important observations can be made from the data represented in FIG. 5. First, free BIS-1 had very little effect on the expression levels of any of the tested markers. This may be because as a highly charged and polar molecule, BIS-1 may not efficiently pass through the cell membrane and interact with effector proteins in the interior of cells. Conversely, MAD-BIS-1 actively transports BIS-1 into cell through its interaction with CD206 and release of its payload in the mildly acidic conditions of endosomes. MAD-BIS-1 did significantly alter the expression of 6 of the evaluated surface markers. CD206 and CD163, which are frequently associated with an M2-like phenotype, were significantly reduced in expression by more than half. Conversely, CD80 and CD86, which bind to CD28 on T-cell and activate T-cells, are frequently thought of as indicative of an M1-like phenotype. Both CD80 and CD86 are significantly increased in expression by treatment with MAD-BIS-1.

Also, importantly, is the observation that MAD-BIS-1 significantly reduced the expression of SIRPα. SIRPα is the receptor for CD47. CD47 is frequently expressed on many kinds of cells including many cancer cells. CD47 is called the "don't eat me" signal. When CD47 binds to SIRPα, it suppresses the phagocytic response in macrophages. A decrease in expression of SIRPα may be indicative of a more M1-like proinflammatory macrophage phenotype in which macrophages are more likely to phagocytize cancer cells. Expression of PD-1 is increased by MAD-BIS-1. However, the very low levels of PD-1 expression in macrophages treated with the saline control suggests that the modest but significant increase in PD-1 expression induced by MAD-BIS-1 may have limited phenotypic significance.

Overall, the decreased expression of CD206, CD163 and SIRPα coupled with the increased expression of CD80 and CD86, indicates that treatment with MAD-BIS-1 stimulates macrophages to adopt a more M1-like proinflammatory and anti-tumor phenotype. It is also important to note that the observed changes in macrophage phenotype could not be replicated by free BIS-1 at any dose, indicating that BIS-1 activity was dependent on intracellular transport mediated by MAD binding to CD206 and possibly other cycling pattern recognition receptors.

Example 3: Bisphosphonate 2 (MAD-BIS-2)

MAD-BIS-2 was evaluated in human macrophage culture assays similar to those described in Example 2 with two differences. First, for the changes in cell surface markers chosen for display, the MAD-BIS-2 concentration chosen for comparison was 40 µg/ml rather than 80 µg/ml as was the case of MAN-BIS-1. More importantly, the comparator for MAN-BIS-2 was not free BIS-2 but free zoledronic acid (Zoledronate). Like BIS-1 and BIS-2, zoledronic acid is a nitrogenous bisphosphonate. Zoledronic acid is the most pharmacologically active bisphosphonate drug with regulatory approval. In the data shown in FIG. 6, the phenotypic changes induced by MAD-BIS-2 were compared with equal molar equivalent concentrations of zoledronic acid rather than free BIS-2.

Figure 6:
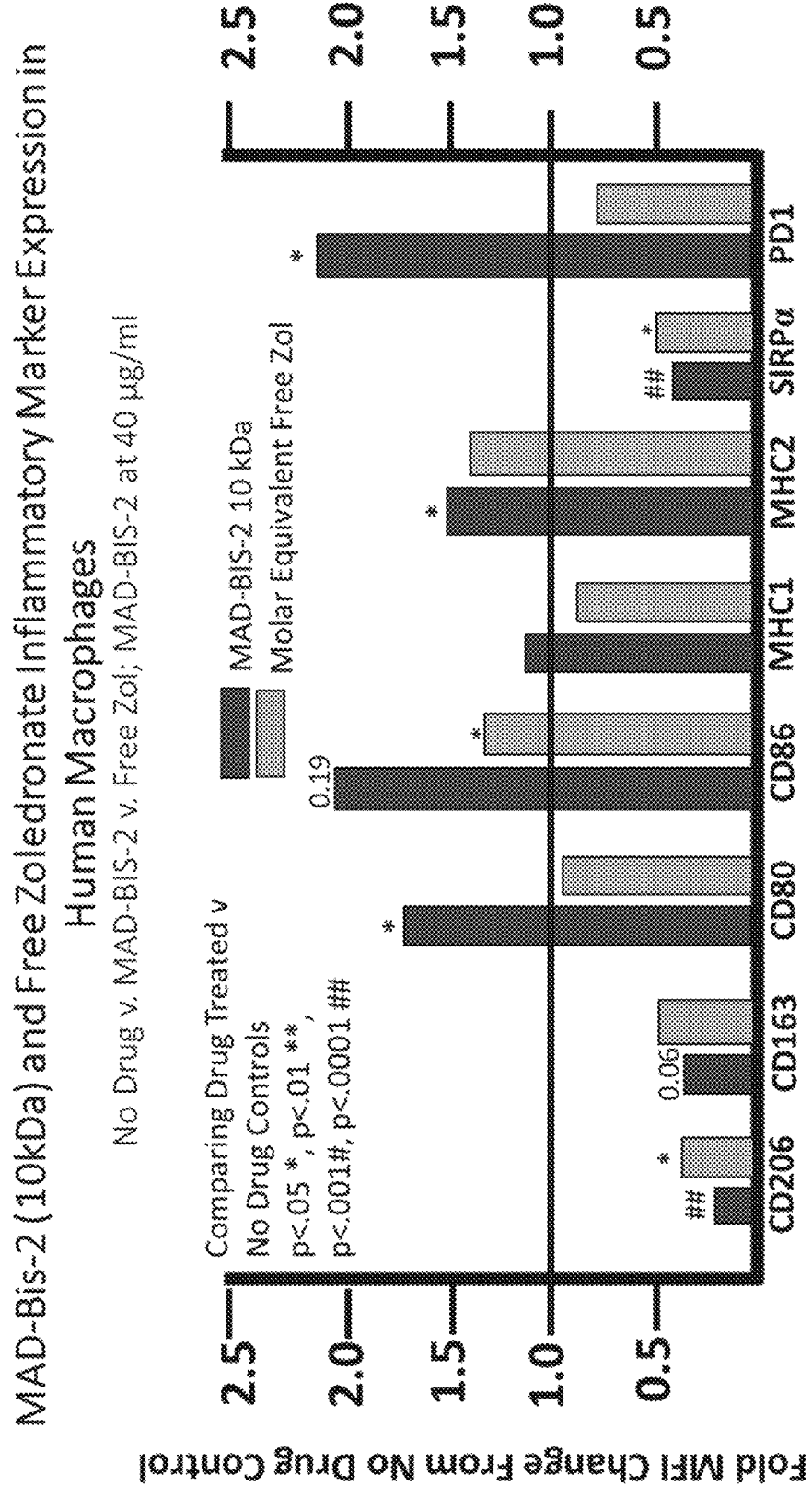
FIG. 6 shows a graph of how the various treatments with either MAN-BIS-2 (10 kDa) or free zoledronic acid affected the level of expression of eight evaluated surface markers, CD206, CD163, CD80, CD86, MHC1, MHC2, SIRPα, and PD1. All experiments were run in triplicate with macrophages from 3 human donors.
Figure 7:
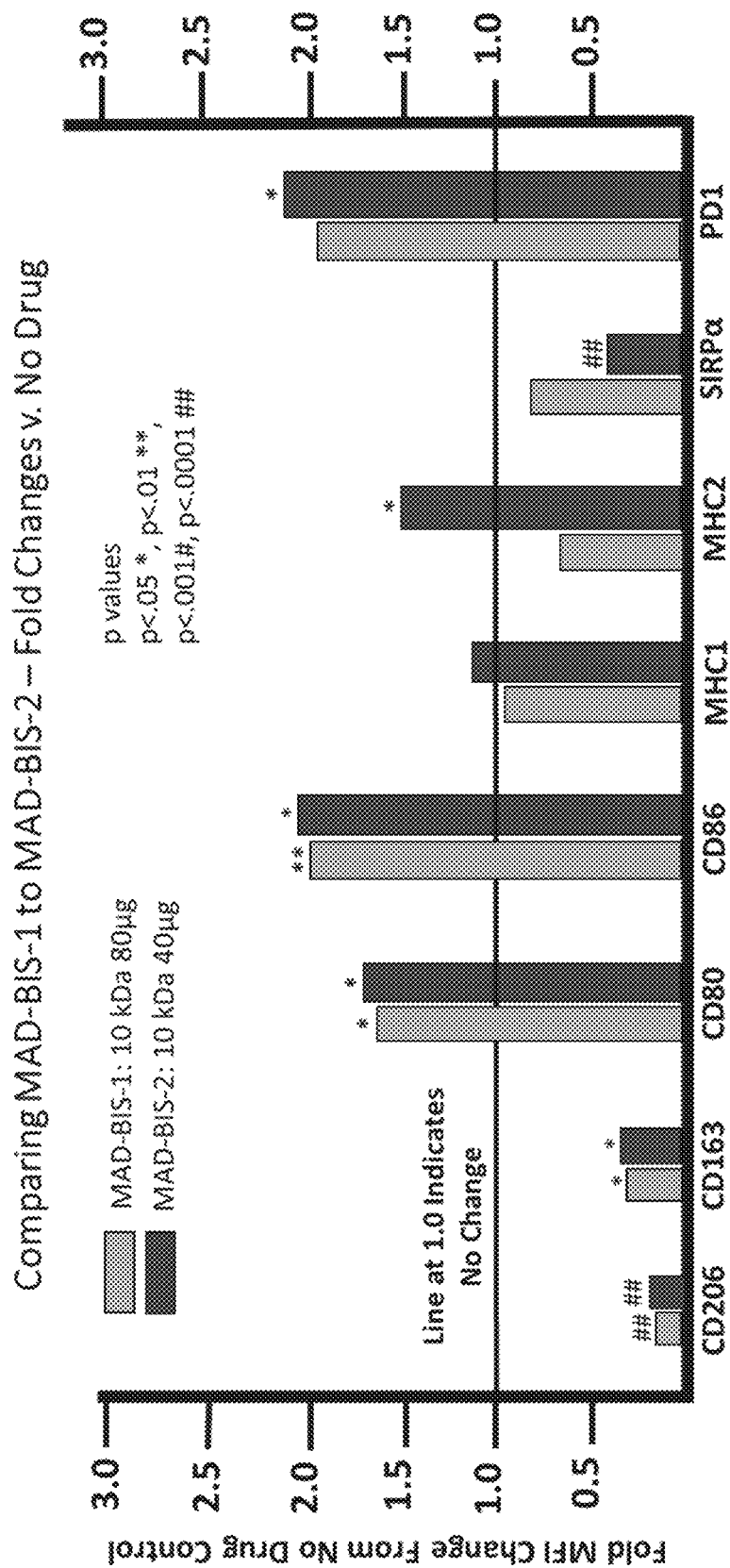
FIG. 7 shows a graph of the comparison between the affects of MAD-BIS-1 to MAD-BIS-2 on the expression of eight evaluated surface markers, CD206, CD163, CD80, CD86, MHC1, MHC2, SIRPα, and PD1. All experiments were run in triplicate with macrophages from 3 human donors.

As shown in FIG. 6, the changes in surface marker expression induced by MAN-BIS-2 were similar to those induced by MAN-BIS-1, with significant decreases in expression levels of CD206, CD163, and SIRPα, and increases in expression levels of CD80, CD86, and PD-1. One difference was that MAN-BIS-2 induced a modest increase in expression of MHC2 while MAN-BIS-1 induced a small decrease in MHC2. A direct comparison of the changes in surface marker expression induced by MAD-BIS-1 (80 µg/ml) and MAD-BIS-2 (40 µg/ml) is shown in FIG. 7. While the changes in surface marker expression levels induced by MAD-BIS-1 and MAD-BIS-2 are not identical, they are sufficiently similar to suggest that the two bisphosphonate constructs have similar if not identical pharmacological mechanisms of action. As was the case with MAD-BIS-1, MAD-BIS-2 modified the phenotype of human macrophages to become more M1-like with MAD-BIS-2 being possibly more pharmacologically active than MAD-BIS-1.

As shown in FIG. 6, free zoledronic acid had observed phenotypic effects on the treated macrophages similar to the effects seen for MAN-BIS-1 and MAN-BIS-2. Free zoledronic acid caused decreased expression of CD206, CD163, and SIRPα and increased expression of CD86 and (non-significantly) MHC2; however, while these changes were qualitatively similar to the changes in marker expressions seen with treatment with the MAD-BIS-2 construct, the changes observed when treating macrophages with free zoledronic acid were quantitatively smaller and less statistically significant. The mechanism by which free zoledronate enters the macrophages to mediate these modest changes in surface marker expression is uncertain but likely results from small quantities of drug ingested during pinocytosis. It is likely that zoledronic acid is more pharmacologically active once it has gained intracellular access, but this activity is tempered by the inability of highly charged zoledronic acid to pass through cellular membranes to gain access to intracellular pharmacological targets. Conversely, BIS-2 may be less pharmacologically active compared to zoledronic acid but can achieve higher intracellular concentrations due to active intracellular transport mediated by CD206 when attached to MADs.

Figure 8:
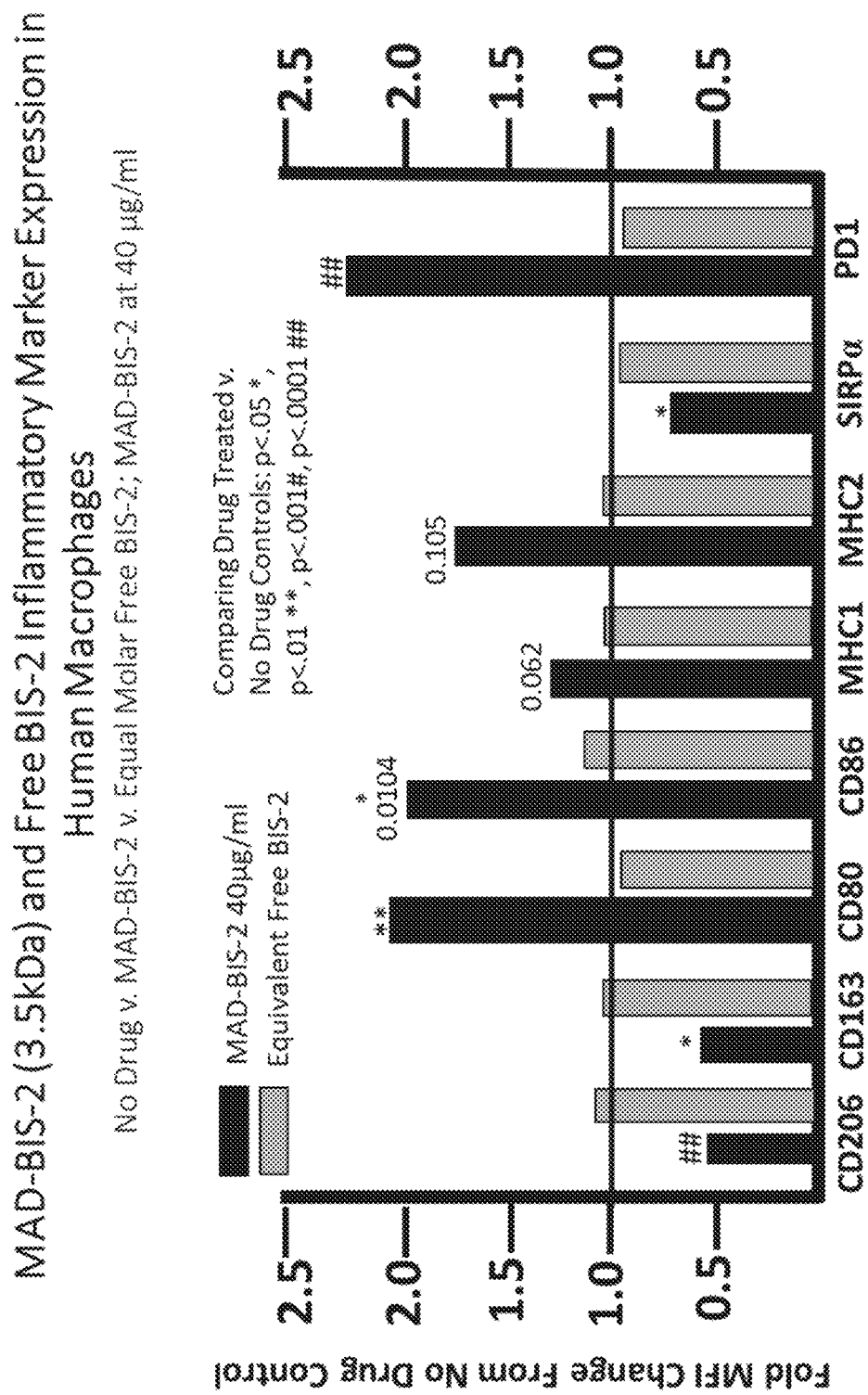
FIG. 8 shows a graph of how the various treatments with either MAN-BIS-2 (3.5 kDa) or free BIS-2 altered inflammatory marker expression, including expression of eight evaluated surface markers, CD206, CD163, CD80, CD86, MHC1, MHC2, SIRPα, and PD1. All experiments were run in triplicate with macrophages from 3 human donors.

FIG. 8 shows the results of an experiment that was similar to that shown in FIG. 6 except that activity of MAD-BIS-2 was compared to free BIS-2 instead of free zoledronic acid and the MAD-BIS-2 construct was constructed on a smaller dextran backbone with a starting molecular weight (Mw) of 3.5 kDa compared to MAD-BIS-2 construct providing the results shown in FIG. 6, which had a starting molecular weight (Mw) of 10 kDa. Otherwise, the two MAD-BIS-2 constructs have similar molecular structures. On a per mass basis, the two MAD-BIS-2 constructs carried similar masses of BIS-2 payloads. After completion of syntheses, the final molecular weights (Mw) of MAD-BIS-2 (10 kDa dextran) and MAD-BIS-2 (3.5 kDa backbone) were about 18-22 kDa and 8-11 kDa, respectively. The results shown in FIG. 8 report that the MAD-BIS-2 (3.5) construct induced the decreased expression of CD206, CD163, and SIRPα, and the increased expression of CD80, CD86, and MHC2. Importantly, as was the case with BIS-1, free BIS-2 did not alter the expression level of any of the evaluated surface markers, indicating that its intracellular internalization was also dependent on attachment to a MAD drug delivery vehicle.

Figure 9:
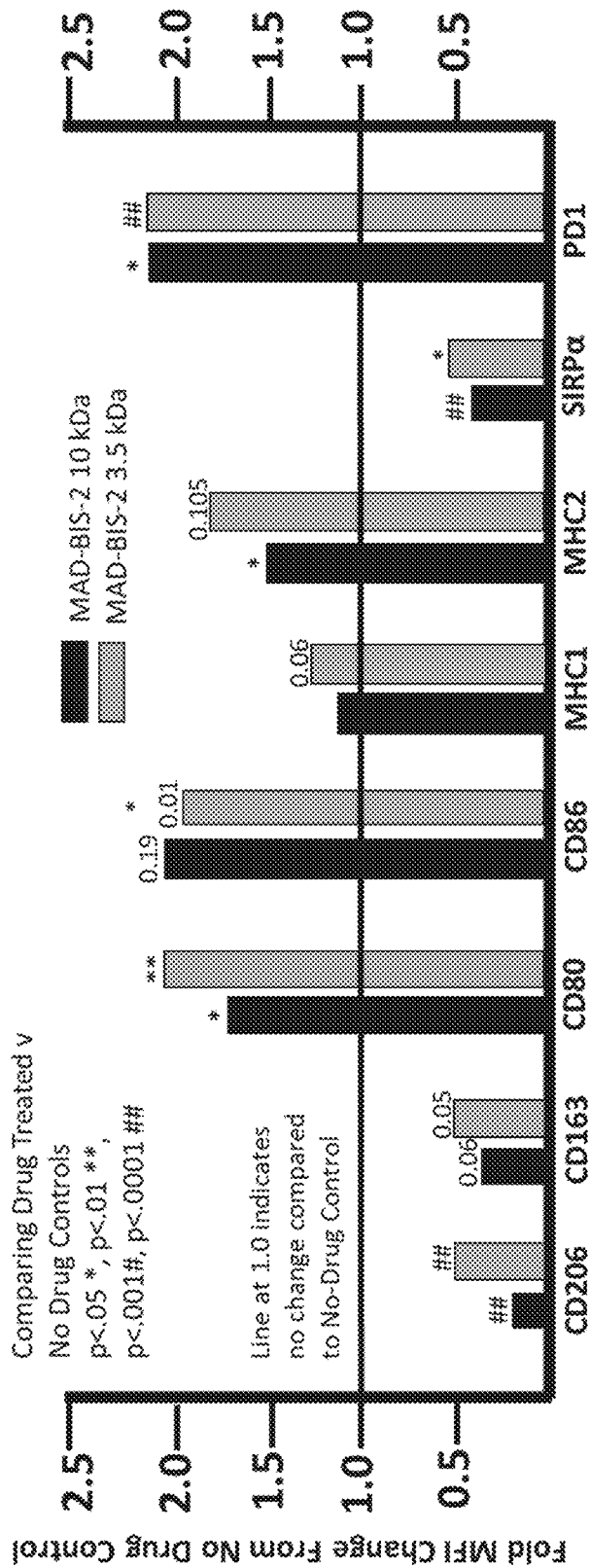
FIG. 9 shows a graph of how the various treatments with either MAN-BIS-2 (10 kDa) or MAN-BIS-2 (3.5 kDa) altered inflammatory marker expression, including expression of eight evaluated surface markers, CD206, CD163, CD80, CD86, MHC1, MHC2, SIRPα, and PD1. All experiments were run in triplicate with macrophages from 3 human donors.

FIG. 9 shows a direct comparison of the surface marker expression results aggregated from the results shown in FIG. 6 (MAD-BIS-2, 10 kDa dextran) and FIG. 8 (MAD-BIS-2, 3.5 kDa dextran). FIG. 9 demonstrates that the two MAD-BIS-2 constructs—that vary predominately only by the size of their initial dextran backbones and final molecular weights—induce comparable changes in macrophage surface marker expressions (i.e., phenotypes) that are statistically nearly the same. The pharmacological effects of MAD-BIS-2 constructs are independent of the size (Mw) of the MAD-BIS-2 constructs or the initial sizes of their dextran backbones. One would expect that MAD-BIS-2 constructs built on dextran backbones that were smaller than 3.5 kDa, between 3.5 kDa and 10 kDa, or larger than 10 kDa would have similar pharmacological effects as long as they possessed sufficient numbers of mannose moieties to bind avidly to CD206. Furthermore, because MAD-BIS-1, MAD-BIS-2, and zoledronic acid are all nitrogenous bisphosphonates and all induce similar patterns of pharmacological effects on macrophage surface marker expression and macrophage phenotypes, one would expect that a wide variety of other nitrogenous bisphosphonate drugs, when delivered to CD206 expressing cells such as macrophages linked to a MAD construct via a degradable linker, would also induce similar patterns of pharmacological effects on macrophage surface marker expression and macrophage phenotypes. While other MAD constructs carrying other nitrogenous bisphosphonates may have greater or lesser pharmacological activity compared to MAD-BIS-1 or MAD-BIS-2, all would be expected to induce similar patterns of changes in surface marker expressions and similarly shift the phenotype of macrophages away from a M2-like immunosuppressive and protumor phenotype and towards a more M1-like anti-tumor phenotype.

The exemplary mannosylated dextran constructs evaluated have several important attributes of note. They are both nitrogenous bisphosphonates. They both altered the phenotype of human macrophages to be more MI-like. This indicates that the MAD-BIS constructs can be used to adjust the tumor immune microenvironment to be less immunosuppressive and tumor promoting, and more pro-inflammatory and anti-tumor. Further, both MAD-BIS constructs significantly reduced the expression of SIRPα, indicating the MAD-BIS treated TAMs may be more likely to phagocytize tumor cells. In addition, and as demonstrated by experiments with MAD-BIS-2 constructs, the pharmacological activity of MAD-BIS constructs are independent of the size of the MAD component of the construct.

The results further suggest that the MAD-BIS constructs can improve the efficacy of other anti-cancer therapies, such as radiation therapies, cytotoxic therapies, and immunotherapies, by shifting the immune microenvironment of a tumor to be less immunosuppressive and pro-tumor.

Further benefits of the MAD-BIS constructs include targeting to CD206 expressing cells such as macrophages and dendritic cells, thus reducing off target toxicities. The MAD-BIS constructs can deliver their payloads internally to their targeted CD206 expressing cells, overcoming challenges related to limitations of highly charged and polar molecules, such as bisphosphonates, to pass through the cell membrane and gain access to intracellular drug targets. As demonstrated within the examples, MAD-BIS constructs are at least as pharmacologically active or more so than free zoledronic acid, the most active drug in the bisphosphonate drug class.

The disclosures being thus described, it will be obvious that the same may be varied in many ways. Such variations are not to be regarded as a departure from the spirit and scope of the disclosures and all such modifications are intended to be included within the scope of the following claims.

What is claimed is:

1. A bisphosphonate compound of Formula (II):

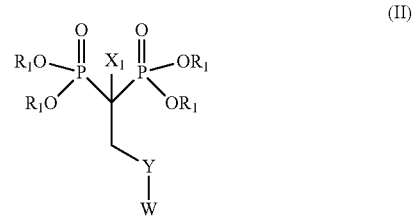

(II)

wherein
$R_1$ are each independently H, a positively-charged counter ion, a substituted or unsubstituted, linear or branched $C_1$-$C_6$ alkyl group, or an acyloxyalkyl group;
$X_1$ is H or a $C_1$ alkyl group;
Y is NH or absent; and
W is an imidazole or a thiazole substituted with a $C_1$ alkyl group, wherein W is further substituted with a carbonyl group that is either a ketone group, or the carbonyl group is combined with an acylhydrazide to form a bisphosphonate compound modified with a hydrazone moiety.

2. The compound of claim 1, wherein W is an imidazole, the carbonyl group is a ketone group, Y is absent, and $X_1$ is a $C_1$ alkyl group.

3. A bisphosphonate compound of Formula (III):

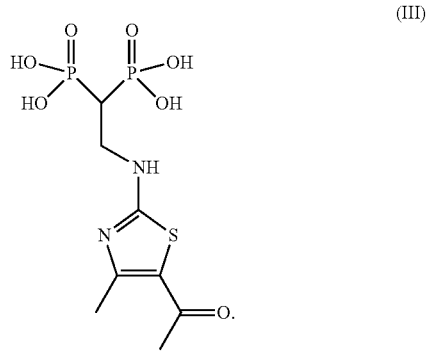 [SMILES: CC(=O)c1sc(NCC(P(=O)(O)O)P(=O)(O)O)nc1C]

(III)

4. The compound of claim 1, wherein the compound has the following formula (IV):

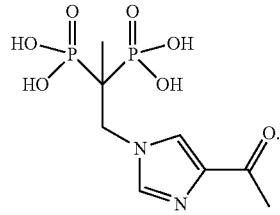
(IV)

5. The compound of claim 1, wherein the carbonyl group is combined with an acylhydrazide to form a bisphosphonate compound modified with a hydrazone moiety.

6. The compound of claim 5, wherein the acylhydrazide has the following structure:

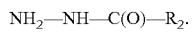

7. The compound of claim 5, wherein the hydrazone moiety has the following structure:

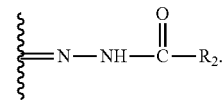

8. The compound of claim 7, wherein $R_2$ comprises $-R_4-SH$, wherein $R_4$ is a substituted or unsubstituted, linear or branched $C_1$-$C_{12}$ alkyl, alkenyl, alkynyl, or aromatic group.

9. The compound of claim 7, wherein $R_2$ comprises $-(CH_2)_2SH$.

10. The compound of claim 5, wherein the compound has the following formula (V):

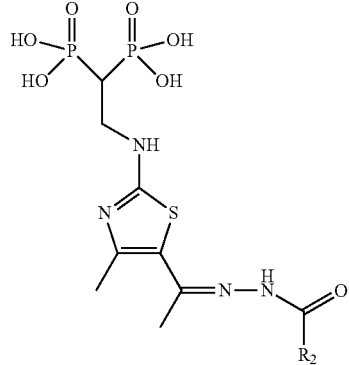
(V)

wherein $R_2$ comprises $-R_4-SH$, wherein $R_4$ is a substituted or unsubstituted, linear or branched $C_1$-$C_{12}$ alkyl, alkenyl, alkynyl, or aromatic group.

11. The compound of claim 10, wherein $R_2$ comprises $-(CH_2)_2SH$.

12. The compound of claim 5, wherein the compound has the following formula (VI):

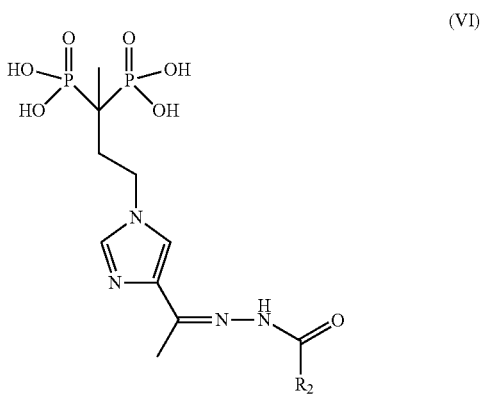
(VI)

wherein $R_2$ comprises $-R_4-SH$, wherein $R_4$ is a substituted or unsubstituted, linear or branched $C_1$-$C_{12}$ alkyl, alkenyl, alkynyl, or aromatic group.

13. The compound of claim 12, wherein $R_2$ comprises $-(CH_2)_2SH$.

* * * * *